United States Patent [19]
Downey et al.

[11] Patent Number: 5,562,095
[45] Date of Patent: * Oct. 8, 1996

[54] THREE DIMENSIONAL ULTRASOUND IMAGING SYSTEM

[75] Inventors: Donal Downey; Aaron Fenster; John Miller; Shidong Tong, all of London, Canada

[73] Assignees: Victoria Hospital Corporation; London Health Assoc., Ontario, Canada

[ * ] Notice: The term of this patent shall not extend beyond the expiration date of Pat. No. 5,454,371.

[21] Appl. No.: 419,049

[22] Filed: Apr. 4, 1995

Related U.S. Application Data

[63] Continuation of Ser. No. 158,267, Nov. 29, 1993, abandoned.

[30] Foreign Application Priority Data

Dec. 24, 1992 [GB] United Kingdom .................... 9226935
Mar. 1, 1993 [GB] United Kingdom .................... 9304112

[51] Int. Cl.$^6$ ..................................................... A61B 8/00
[52] U.S. Cl. ..................................................... 128/660.09
[58] Field of Search ...................... 128/660.05, 660.07, 128/660.08, 660.09, 660.10, 661.01, 916; 364/413.22, 413.19; 395/162, 163, 119; 382/6, 44, 45, 46

[56] References Cited

U.S. PATENT DOCUMENTS 5,329,929 7/1994 Sato et al. .......................... 128/660.05
5,454,371 10/1995 Fenster et al. ...................... 128/660.07

*Primary Examiner*—George Manuel

[57] ABSTRACT

A 3-D ultrasound imaging system for the eye, prostate and other organs, comprising an assembly onto which an ultrasound probe may be mounted, a motor and drive for either rotating or scanning the probe relative to the human organ under investigation, and a computer for executing proprietary software for controlling movement of the assembly to rotate or scan the probe. Ultrasound signals from the probe are processed via a clinical ultrasound machine for generating multiple images of the organ. The proprietary software being executed on the computer collects the 2-D ultrasound images of the clinical ultrasound machine and reconstructs these images to form a 3-D display which can be viewed and manipulated in real time, or stored for later retrieval.

28 Claims, 24 Drawing Sheets

Transformation of I(x,y,z) to R(x,y,z)

I(x,y,z) --------→ R(x,y,z)

Transformation of I(x,y,z) to R(x,y,z)

the last z-slice of I(x,y,z)

I(x,y,z) --------→ R(x,y,z)

○ Pixels of $A(x,y)$
● Pixel of $T(x,y)$
⊘ Neighbors of $p(x_0,y_0)$ in $A(x,y)$
* $r_i \leq r \leq r_{i+1}$

THREE DIMENSIONAL ULTRASOUND IMAGING SYSTEM

This application is a continuation of application Ser. No. 08/158,267, filed Nov. 29, 1993, abandoned.

FIELD OF THE INVENTION

This invention relates in general to medical diagnostic equipment and more particularly to a system for three dimensional (3-D) ultrasound imaging of human organs such as the eye, prostate, and other organs suitable for ultrasound imaging.

BACKGROUND OF THE INVENTION

Clinical ultrasound diagnostic equipment is well known in the medical arts for viewing internal human organs. For example, opthamologists and radiologists often require images of the eye for investigating eye maladies and for making volumetric measurements. In diagnosing prostate cancer, a diagnostician uses transrectal ultrasound (TRUS) to identify whether lesions are present, and determines the location, size and extent of the lesions. However, such prior art ultrasound devices produce only 2-D images whereas the anatomies under investigation are three-dimensional. Hence, the diagnostician must interpret multiple images and integrate them in his or her mind to develop a 3-D impression of the anatomy and pathology under examination. This practice, although routine, is often time consuming and inefficient, and creates the potential for non-optimal diagnosis, and non-optimal staging of disease.

Also, the ultrasound image in prior art 2-D imagers represents a single plane approximately 1 mm thick and at an arbitrary angle in the patient's body. Thus, it is generally difficult to localize the image plane in the organ, and very difficult to reproduce a particular image location at some later time.

Prior art ultrasound imaging systems typically comprise a probe for transmitting ultrasound signals into the human body and receiving reflected ultrasound signals therefrom, and a conventional clinical ultrasound machine for receiving and processing analog ultrasound signals from the probe for generating multiple images of the organ.

A number of patents have been issued relating to prior art probes with internal mechanical sensors. Examples of these systems are disclosed in the following U.S. Pat. Nos.: 5,159,931 (Pini); 5,152,294 (Mochizuki et al); 4,819,650 (Goldstein); 4,841,979 (Dow et al) and 4,934,370 (Campbell).

Prior art systems are also known to use encoders for determining the position of the sensors and transmitting that information to a controlling computer. Examples of such systems are disclosed in the following U.S. Pat. Nos.: 5,159,931 (Pini); 5,152,294 (Mochizuki et al); 4,932,414 (Coleman et al); 4,271,706 (Ledley); 4,341,120 (Anderson); 5,078,145 (Furuhata); 5,036,855 (Fry et al); 4,858,613 (Fry et al) and 4,955,365 (Fry et al).

Other patents have issued which provide general background information on the subject of clinical ultrasound imaging systems. U.S. Pat. No. 5,081,993 (Kithey et al), discloses an intravascular probe for insertion into blood vessels. It incorporates an array of crystals surrounding a tube and generates a cross-sectional view. U.S. Pat. No. 4,747,411 (Ledley) discloses a 3-D imaging system which requires the use of stereo eyeglasses. U.S. Pat. No. 4,899,318 (Schlumberger et al) and U.S. Pat. No. 4,028,934 (Sollish) relate to specific methods of stereoscopic 3-D visualization of objects. U.S. Pat. No. 3,555,888 discloses a probe having a single crystal and a mechanical means for moving the single crystal. U.S. Pat. No. 4,564,018 (Hutchison et al) discloses an ultrasonic diagnostic scanner for producing peak signals and count signals responsive generation of the peak signals for identifying a perceptible eye parameter. U.S. Pat. Nos. 4,594,662; 4,562,540 and 4,598,366 relate to 3-D holography. U.S. Pat. No. 4,866,614 (Tam) teaches the use of a plurality of stationary ultrasound beams which are generated on the basis of multiple transducers. PCT application number PCT/EP92/00410 (Technomed International) discloses a treatment probe inserted into the urethra and means for rotating and moving the probe up and down on a stand.

U.S. Pat. No. 4,932,414 (Coleman) is of interest for disclosing an extension of kidney stone acoustic shattering techniques, applied to the eye. In order to see what a surgeon is doing, an ultrasound imaging probe is provided for sweeping out a volume of the eye resulting in a 3-D impression when the volume is swept quickly enough. However, the Colemen Patent does not disclose any means for reconstruction of the 3-D image from the multiplicity of generated 2-D images. Furthermore, the system of Coleman et al teaches the use of an encoder for determining the position of the probe.

SUMMARY OF THE INVENTION

According to the present invention, a 3-D ultrasound imaging system is provided which comprises a universal assembly onto which an ultrasound probe may be mounted. The assembly incorporates a motor and drive for either rotating or scanning the probe relative to the organ under investigation. Ultrasound signals from the probe are processed via a clinical ultrasound machine for generating multiple images of the organ. A computer is provided for executing software for controlling movement of the assembly to rotate or scan the probe, and for collecting the 2-D ultrasound images from the clinical ultrasound machine and re-constructing these images to form a 3-D display.

In essence, the present invention may be characterized by a novel combination of ultrasound probe, clinical ultrasound machine probe assembly and computer for controlling movement of the probe assembly and reconstructing three-dimensional images from a plurality of two-dimensional images obtained from the clinical ultrasound machine. A unique advantage of the present invention is that it is adaptable to any prior art and manufacture of probe, thereby alleviating the prior art requirement for sophisticated probes with internal moving sensors, etc.

BRIEF DESCRIPTION OF THE DRAWINGS

A detailed description of the preferred and alternative embodiments is provided hereinbelow with reference to the following drawings, in which.

DETAILED DESCRIPTION OF THE PREFERRED EMBODIMENT

Figure 1:
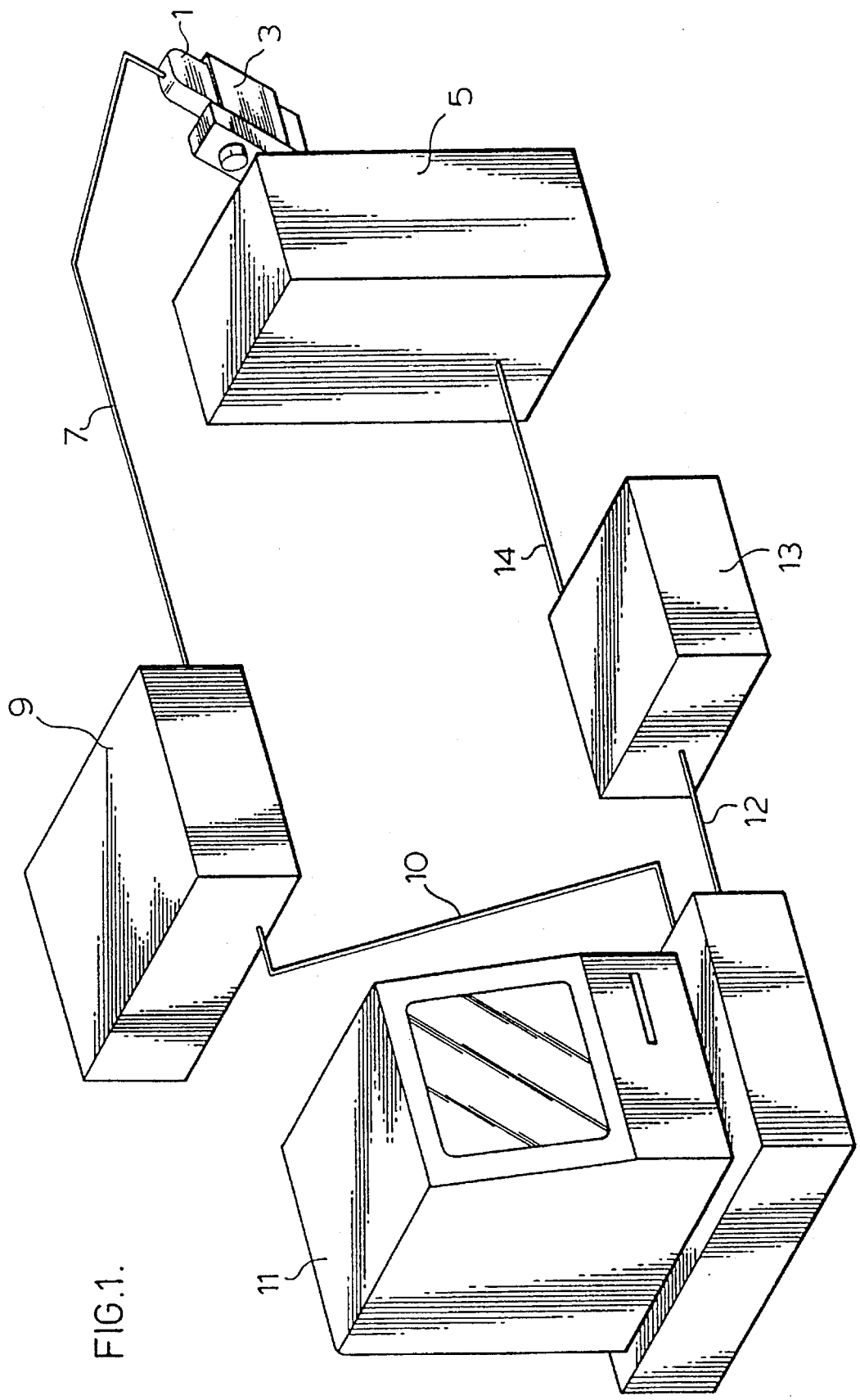
FIG. 1 illustrates the configuration of a 3-D ultrasound imaging system according to the present invention.

With reference to FIG. 1, the overall configuration is illustrated of the 3-D ultrasound imaging system of the present invention. A conventional ultrasound probe 1 is rotated by means of a probe holder 3 which forms part of an assembly 5. The assembly 5 also includes a motor and output shaft for moving the holder 3 and associated probe 1 through a predetermined angular sweep for generating a plurality of images of an organ (not shown) under examination. It is contemplated that the system of the present invention may be used to provide 3-D ultrasound images of the eye, prostate, female breast, heart, arteries and veins, kidney, liver, and other organs suitable for ultrasound imaging. The analog signals from probe 1 are transmitted via a communication line 7 for processing by a conventional clinical ultrasound machine 9. The processed multiple images are transmitted via a communication line 10 from ultrasound machine 9 to a computer 11 which typically incorporates a video-based digitizer (not shown). The series of 2-D images from ultrasound machine 9 are then reconstructed in computer 11 into a single 3-D image for interactive manipulation and display, or into a sequence of 3-D images. The computer 11 also generates control signals to a motor driver 13 via line 12, which in response generates further control signals along line 14 for controlling operation of the assembly 5 to sweep the probe 1.

Figure 2:
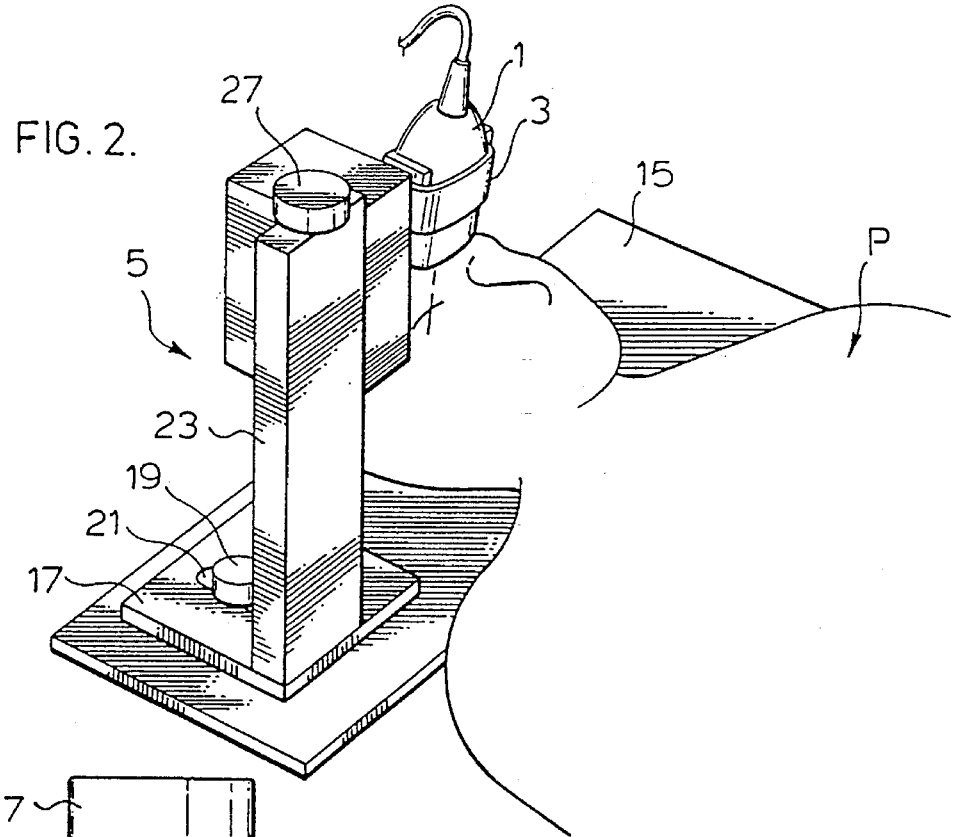
FIG. 2 is a perspective view of an assembly for mounting a conventional ultrasound probe for scanning the human eye or other organs, according to a first embodiment of the invention.
Figure 3:
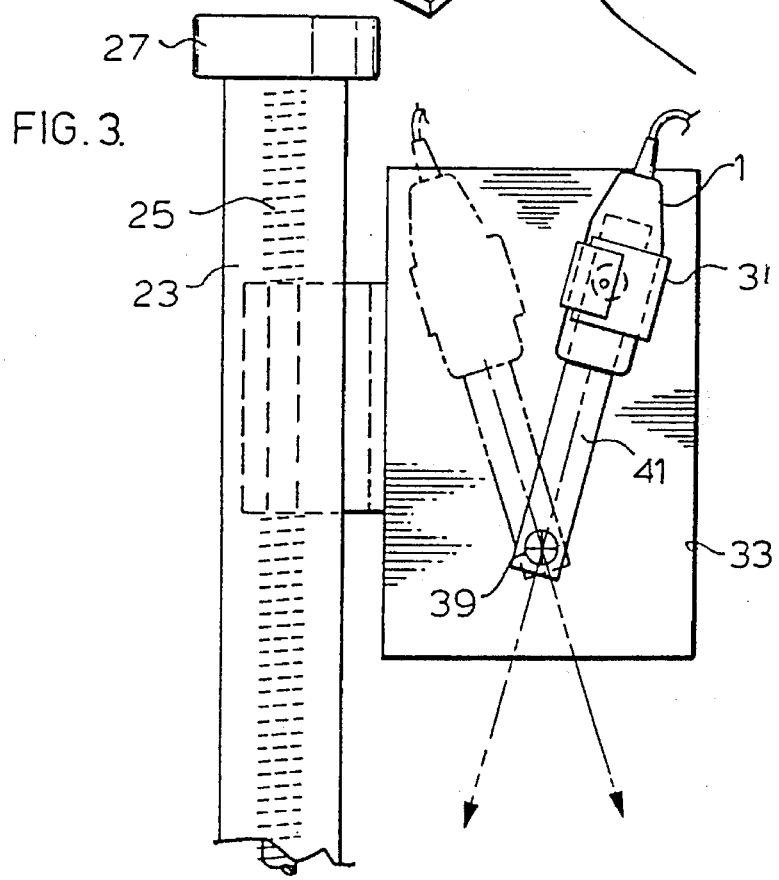
FIG. 3 is a side view of the assembly shown in FIG. 2.
Figure 4:
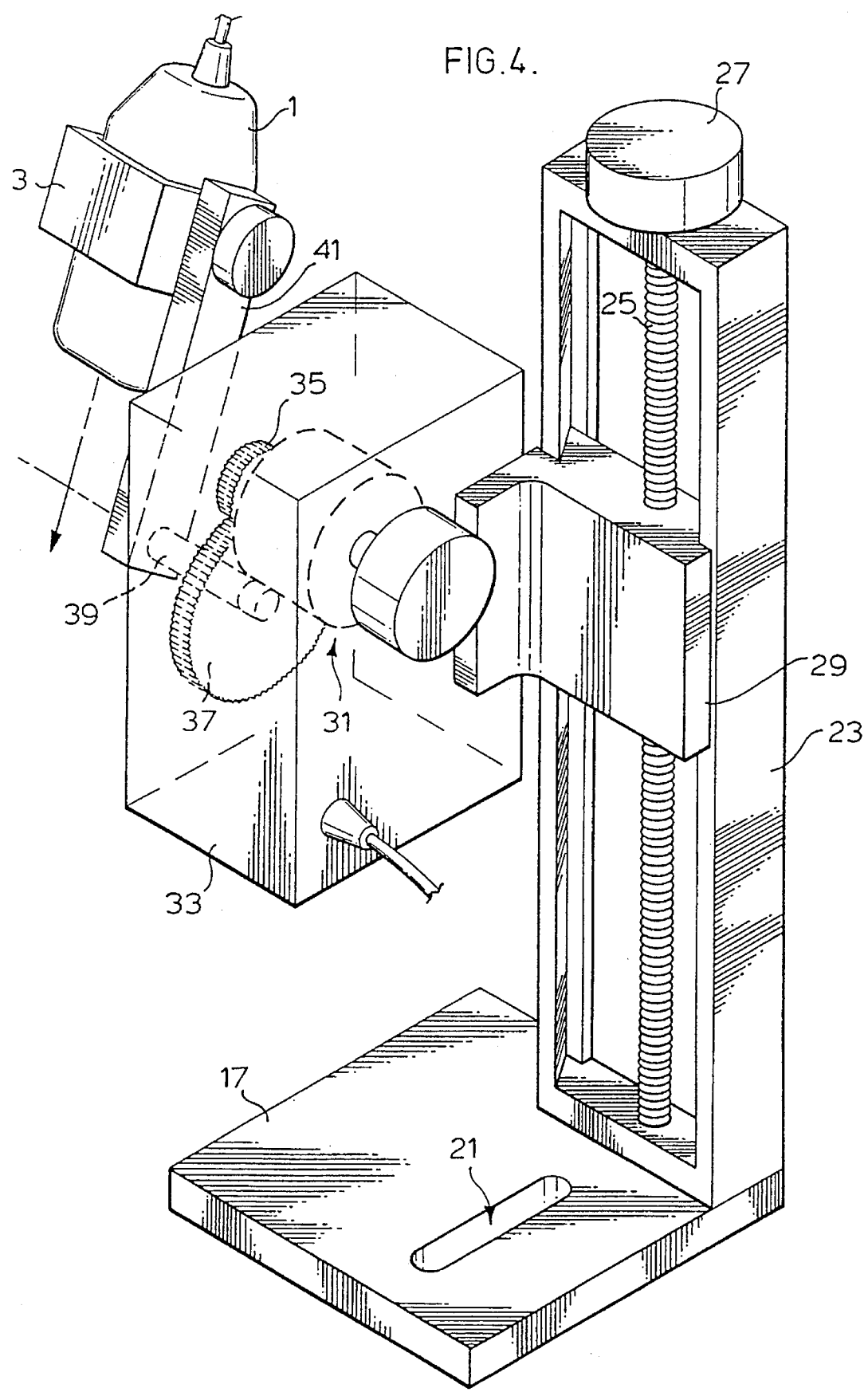
FIG. 4 is a detailed perspective view of the assembly shown in FIGS. 2 and 3.

As discussed above, according to one embodiment of the invention, images of the human eye are scanned and reconstructed in the computer 11. With reference to FIG. 2, an assembly 5 is shown comprising a head support platform 15 for supporting the head of a patient P. A base plate 17 is connected to the supporting platform 15. The horizontal and angular position of the plate 17 may be adjusted by means of the adjustment knob 19 which is threaded to a bolt (not shown) passing through an adjustment slot 21 in the base plate 17. A vertical adjustment member 23 houses a threaded rod 25 to which is connected an adjustment knob 27 at a top end of the vertical adjustment member 23 (see FIGS. 3 and 4). A bracket 29 is connected to vertical adjustment member 23 and has an internal threaded hole through which the adjustment bolt 25 passes, such that the height of the bracket 29 may be adjusted by rotating the knob 27.

A motor 31 is mounted in a motor box 33 which, in turn, is connected to the bracket 29. The motor 31 typically comprises a stepper motor along with gear reduction wheels 35 and 37, and an output shaft 39. An offset arm 41 is connected to the output shaft 39 at one end, while the opposite end of the offset arm 41 is connected to probe holder 3.

In operation, the pivoting offset arm 41 is positioned so that the probe 1 is placed firmly via a coupling gel (see FIG. 10) adjacent the eye of the patient P. Once a desired scan region has been chosen, the motor 31 is actuated thereby causing the arm 41 to sweep across a scanning region while the probe 1 scans the eye to obtain a sequence of images. As discussed in greater detail below, the sequence of images is digitized rapidly and stored in computer 11 (FIG. 1). Preferably, approximately 100 images are collected in a single sweep of approximately 10 second duration, covering a probe scanning angle of approximately 30° (see FIG. 3). The collected images are then reconstructed to form a 3-D volumetric representation of the eye which can then be viewed and manipulated in "real time", either on the monitor of computer 11 or a remote monitor, for diagnostic purposes. As discussed in greater detail below with reference FIGS. 10A and 10B, the embodiment of FIGS. 2–4 sweeps out a 3-D volume of the eye which is an the shape of a sector of a cylinder.

Figure 5:
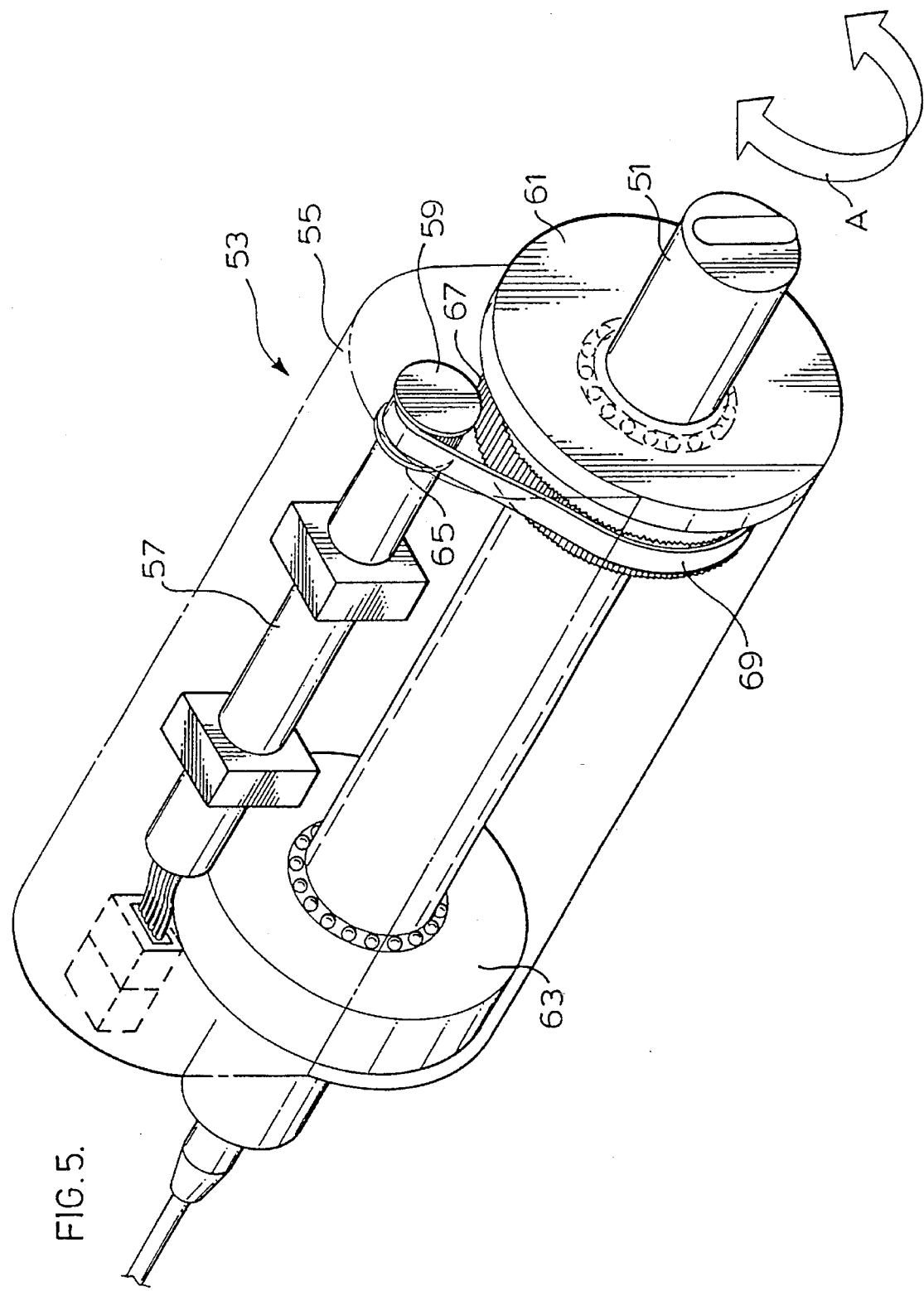
FIG. 5 is a perspective view (partly broken) of an assembly for rotating an end-firing ultrasound probe using axial rotation, according to a second embodiment of the present invention.
Figure 6:
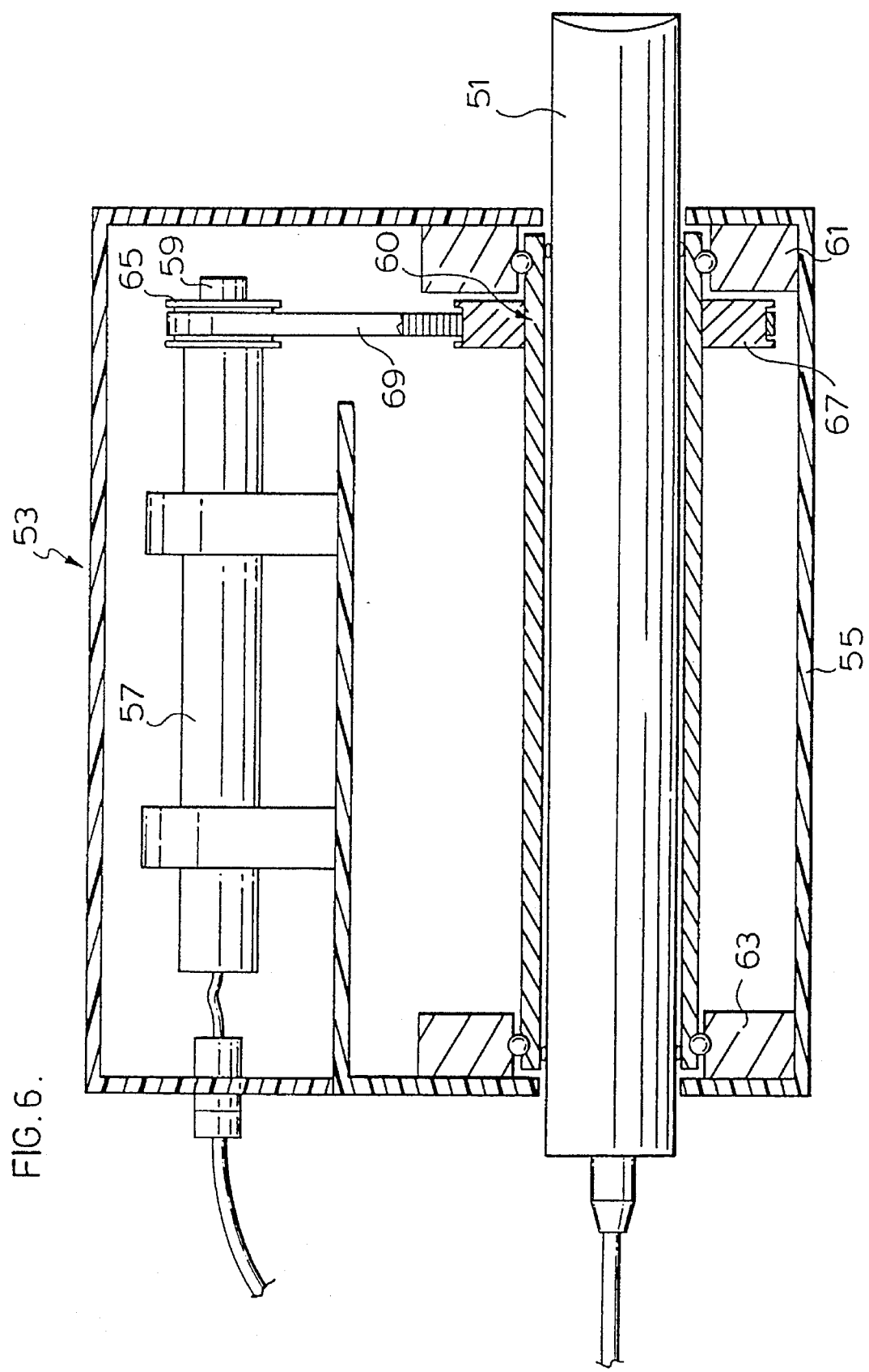
FIG. 6 is a side cross-sectional view of the assembly shown in FIG. 5.

Turning to FIGS. 5 and 6, an alternative embodiment of assembly is shown for axially rotating an end-firing ultrasound probe 51. Thus, the image volume swept out by the probe 51 in the embodiment of FIG. 5 is generally conical, rather than being in the shape of a sector as in the case of the embodiment in FIGS. 2–4. The assembly 53 comprises an external housing which contains a motor 57 with an output shaft 59 extending from one end. The probe 51 is held securely by a barrel 60 supported by a pair of ball bearing mounts 61 and 63. Gear reduction wheels 65 and 67 are connected to the output shaft 59 and barrel 60, respectively, and a belt 69 translates rotary motion of the output shaft 59 to a similar (but gear reduced) rotation of the barrel 60 and consequently also of the probe 51 in a reciprocating circular motion in either direction as illustrated by the arrow A.

The axially rotating embodiment of FIGS. 5 and 6 may be useful for scanning internal organs such as the prostate.

Figure 7:
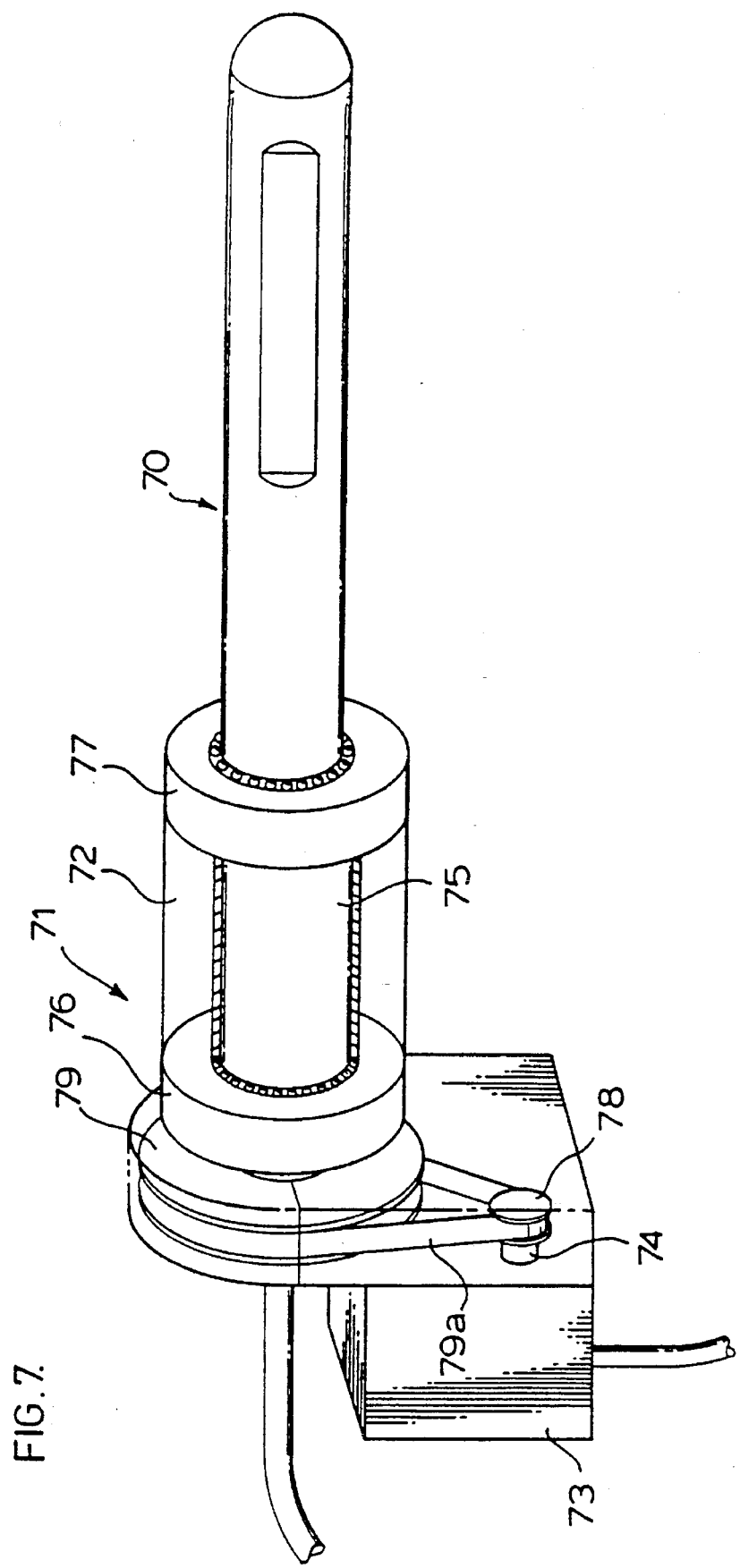
FIG. 7 is a perspective view (partly broken) of an assembly for moving side-firing ultrasound probe using sector rotation, according to a third embodiment of the present invention.

With reference to the embodiment of FIG. 7, an assembly is shown for rotating a side-firing ultrasound probe 70. Thus, the image volume is swept out by the probe 70 in the embodiment of FIG. 7 is generally in the shape of a sector, rather than being conical as in the embodiment of FIGS. 5 and 6. The assembly 71 comprises a probe rotator 72 and motor 73 having an output shaft 74 extending from one end. The probe 70 is held securely by a barrel 75 supported by a pair of ball bearing mounts 76 and 77. Gear reduction wheels 78 and 79 are connected to the output shaft 74 and barrel 75, respectively, and a belt 79a translate rotary motion of the output shaft 74 to a similar (but gear reduced) rotation of the barrel 75 and consequently also of the probe 70 in a circular motion both clockwise and counterclockwise.

The embodiment of FIG. 7 is also useful for scanning internal organs such as the prostate.

Figure 8A:
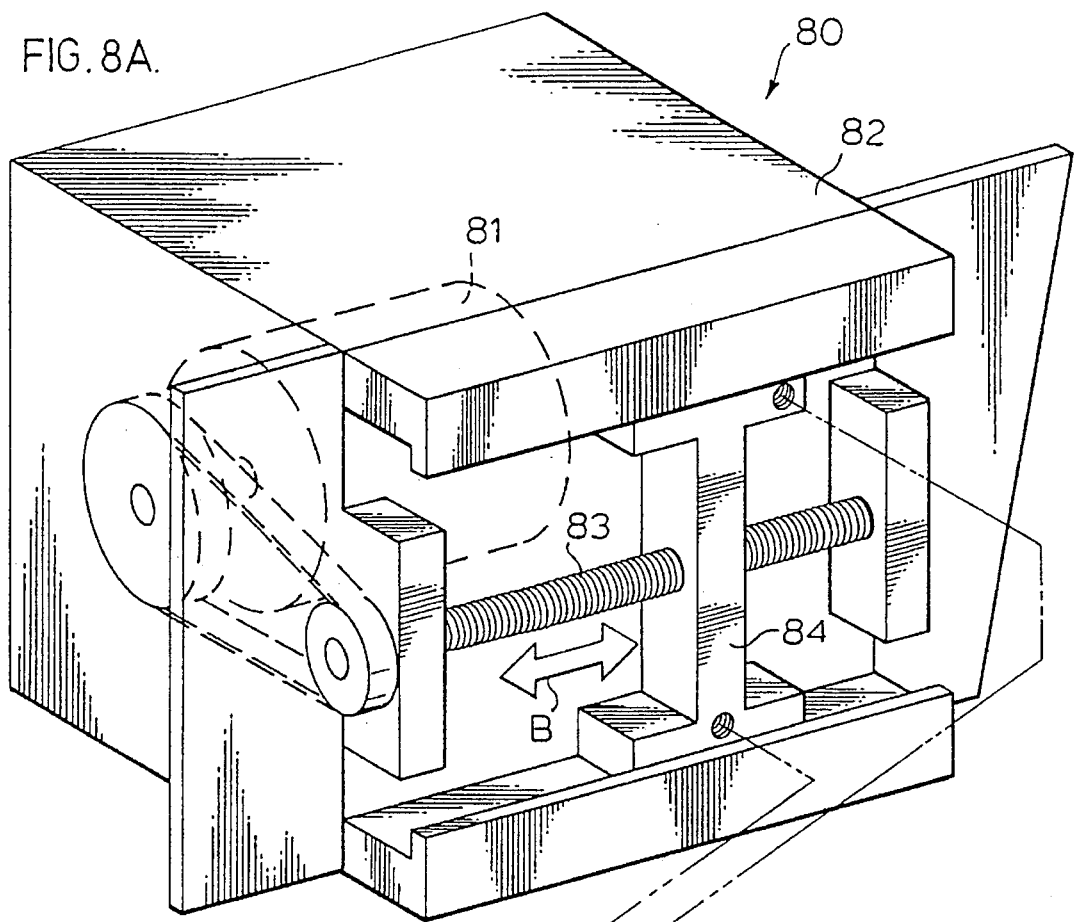
FIG. 8A is a perspective view (partly broken) of a further assembly for moving an ultrasound probe via lateral translation, according to a fourth embodiment of the invention.
Figure 8B:
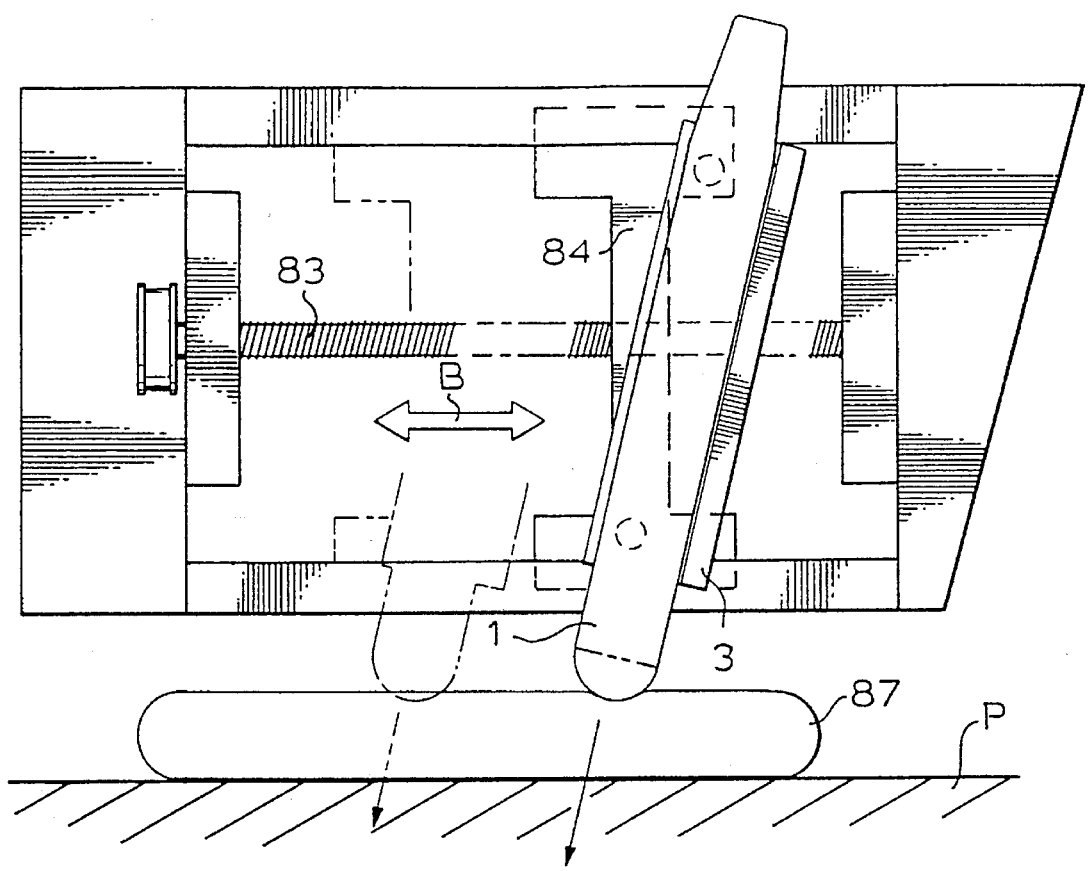
FIG. 8B is a side cross-sectional view of the assembly shown in FIG. 8A.

Turning now to the alternative embodiment of FIGS. 8A and 8B, an assembly 80 is shown comprising a motor 81 within a housing 82. The motor 81 includes gear reduction wheels, belts, etc., which cause a threaded output shaft 83 thereof, to rotate. An I-block 84 is mounted to the output shaft 83 via an internal threaded hole so that the I-block 84 moves according to a linear motion in either direction, as represented by the arrow in FIG. 8A. The holder 3 for probe 1 is connected to I-block 84 via screws 85 and 86. The angle of inclination of the probe 1 relative to the direction of movement, is adjustable via the screw 86.

As shown in FIG. 8B, the assembly of FIGS. 8A and 8B may be used to collect images of an internal organ or lesions such as breast tumors within the trunk of the patient P, there being shown a layer of coupling gel 87 intermediate the probe 1 and the patient P.

Figure 9:
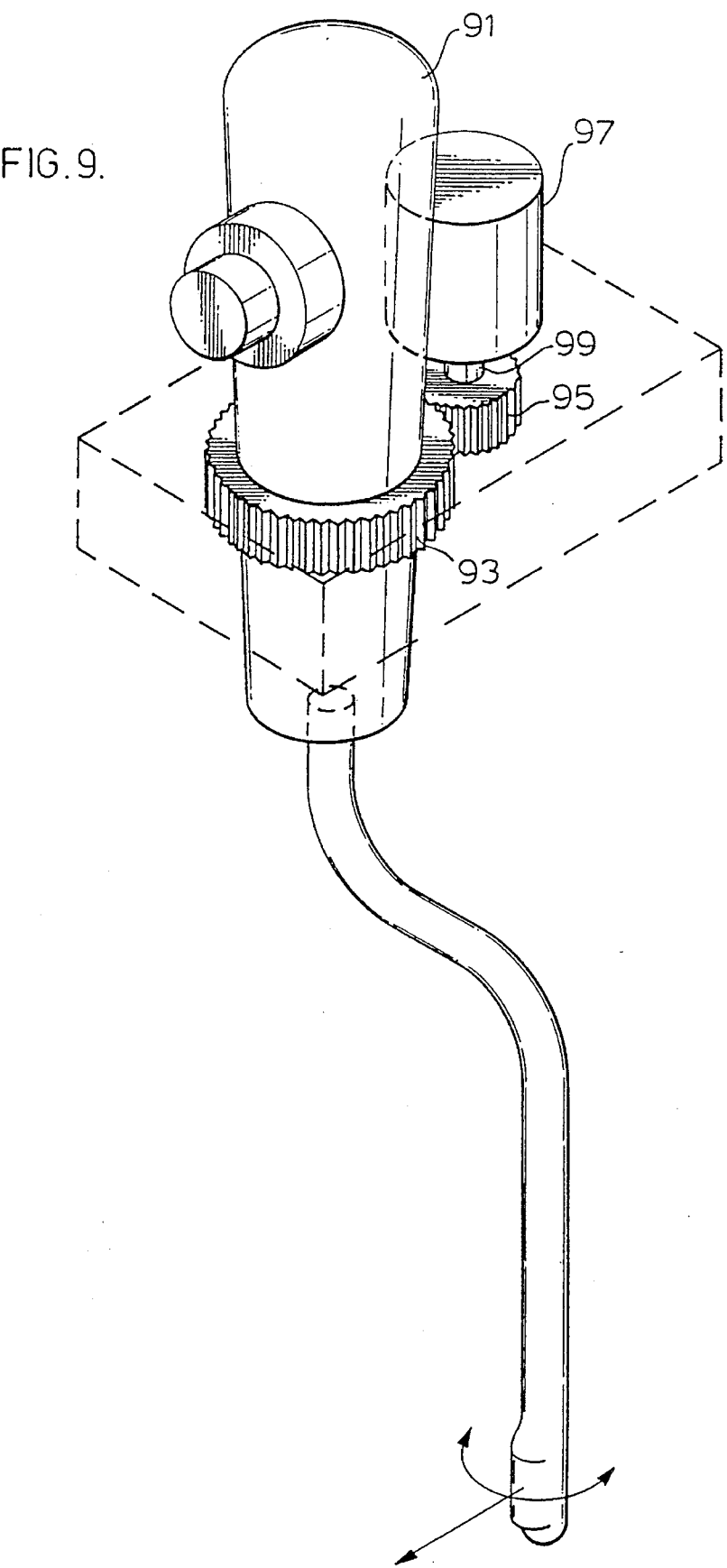
FIG. 9 is a further embodiment of ultrasound probe assembly for rotating the probe via axial rotation.

Turning to yet another alternative embodiment of assembly illustrated in FIG. 9, an ultrasound probe 91 is shown for trans-esophageal imaging of the heart. The probe 91 is mounted within an annular gear-toothed wheel 93 which, in turn, engages a further gear reduction wheel 95 connected to a motor 97 via an output shaft 99 thereof. Upon rotating the output shaft under control of the motor 97, gear wheels 95 and 93 rotate, which causes the ultrasound probe 91 to rotate in consequence.

Although five embodiments of assembly have been illustrated, for diagnostic investigation of the eye, prostate, heart, breast and other internal organs, it is contemplated that additional assemblies may be designed for clinical evaluation of female breasts, the heart, etc. All such embodiments are believed to be within the sphere and scope of the present invention.

Figure 10A:
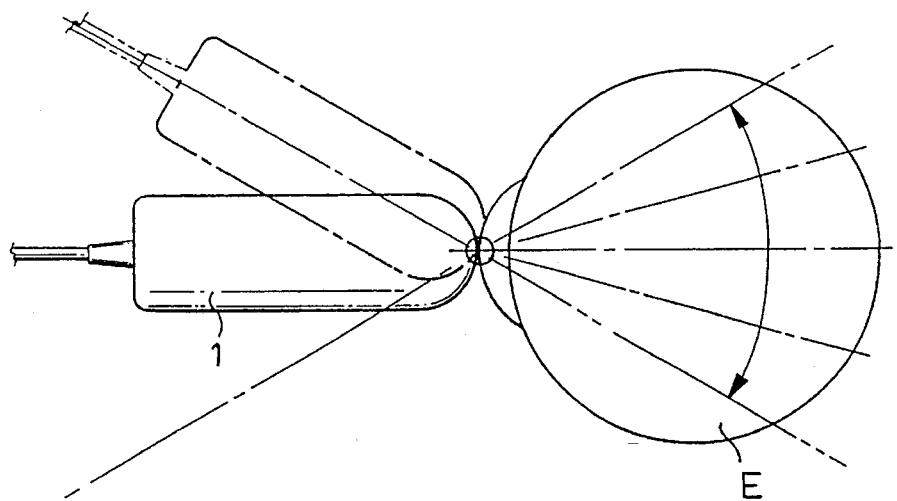
FIGS. 10A–10D illustrate various geometries of probe sweeping movements for imaging the eye, according to the various embodiments of ultrasound probe assemblies.
Figure 10B:
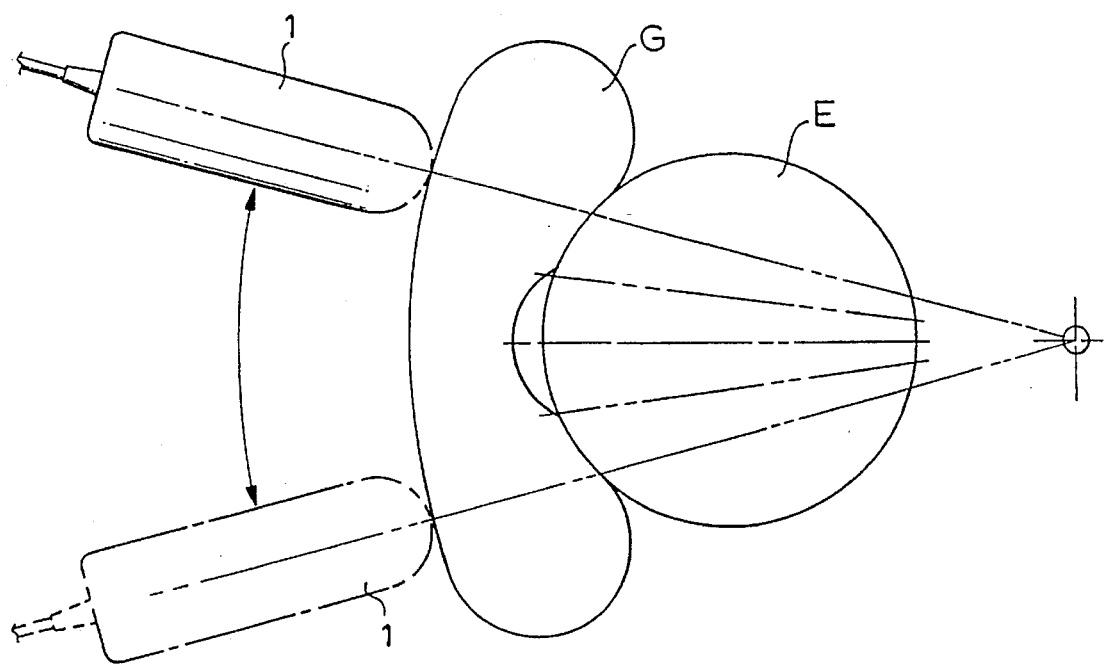
Figure 10C:
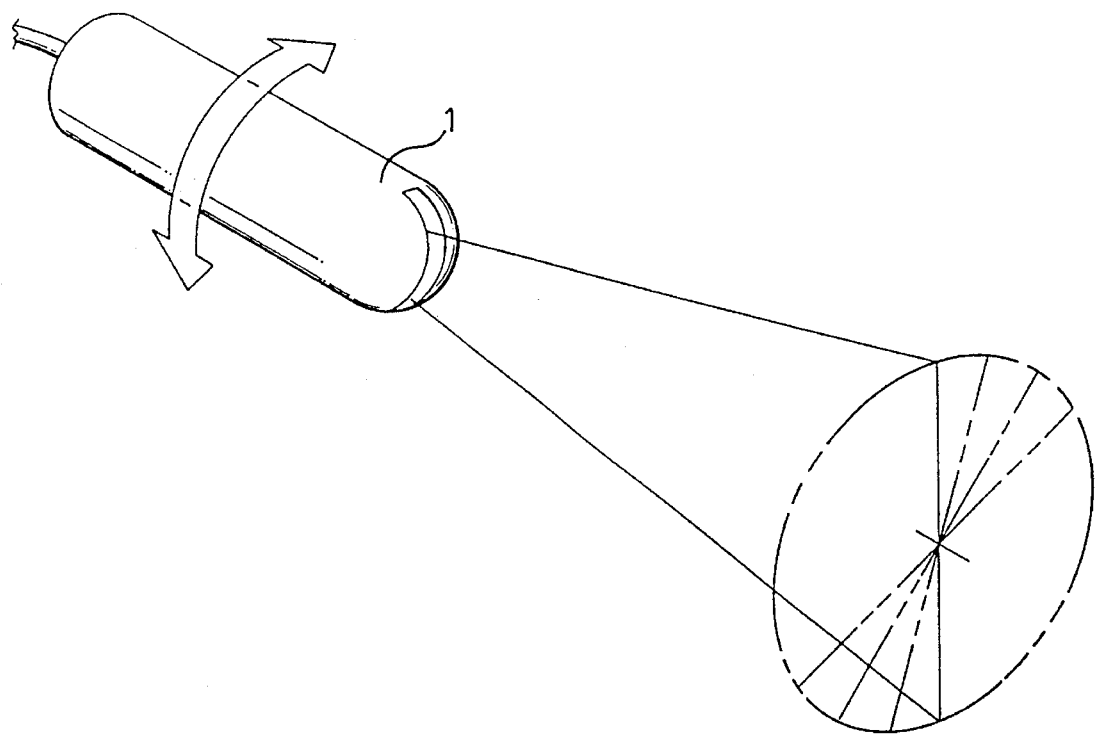
Figure 10D:
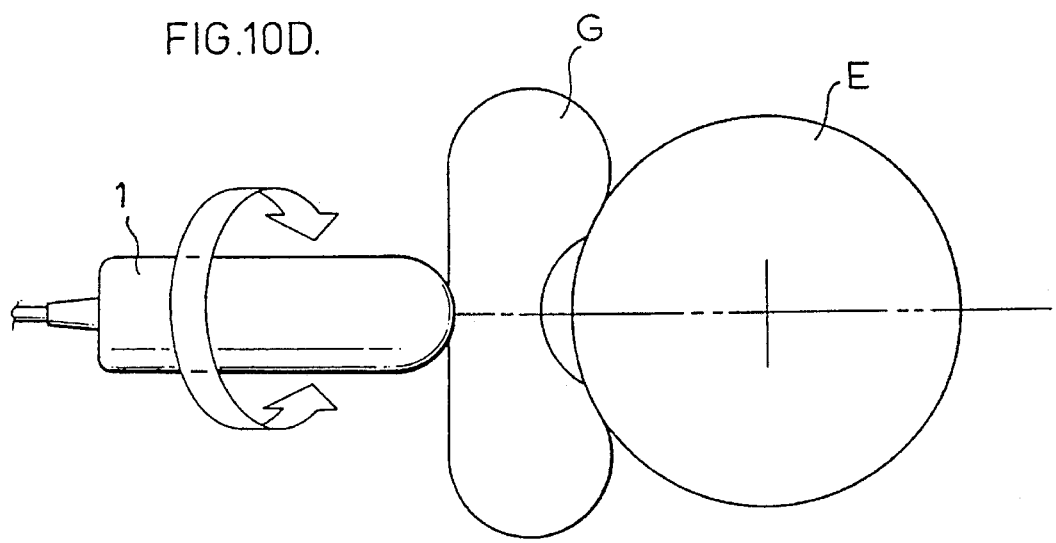

Turning to FIGS. 10A–10D, various scanning geometries are illustrated. In FIG. 10A, the sweeping motion of probe 1 results in a plurality of 2-D images of the eye E conforming to a fan of planes. In FIG. 10B, the probe 1 is separated from the eye E by an acoustic window of gel G such that a fan of two dimensional images is collected wherein the axis of rotation is behind the eye E. The probe rotation mode represented by FIGS. 10A and 10B is referred to herein as "sector" rotation. In FIGS. 10C and 10D, the axis of rotation is longitudinal so as to provide 180° rotation of the probe 1. The probe rotation mode represented by FIGS. 10C and 10D is referred to herein as "axial" rotation.

Figure 11:
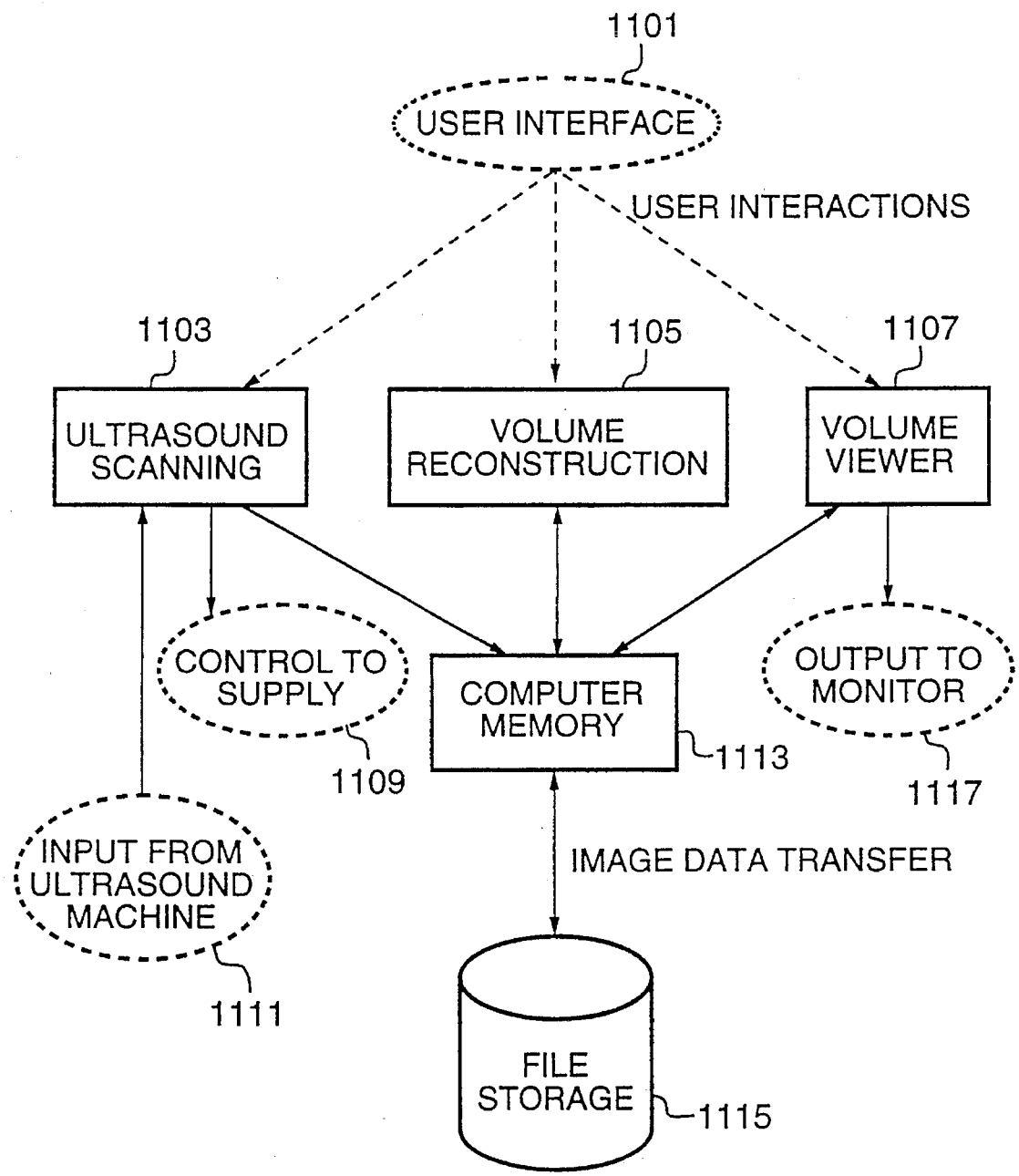
FIG. 11 is block diagram showing functional interconnection of various software modules of the present invention.

The method of reconstructing 3-D images for the geometries of FIGS. 10A–10D is discussed in greater detail below with reference to FIGS. 14–23. However, reference is made firstly to the block diagram of FIG. 11 which shows the overall system functionality of the present invention. A user interface 1101 is provided in the form of a mouse, keyboard or other input to the computer 11 (FIG. 1) and software. The software operating within the computer 11 is divided into various functional modules, as follows: ultrasound scanning module 1103, volume reconstruction module 1105 and volume viewing module 1107. In the case of ultrasound scanning 1103, commands 1109 may be sent to control the probe assembly, (e.g. assembly 5 in FIGS. 2–4, assembly 53 in FIGS. 5 and 6, or assembly 71 in FIGS. 7 and 8 via the master controller 13 (FIG. 1)). A succession of 2-D images from the ultrasound probe 1 are transmitted from clinical ultrasound machine 9 via line 10 as an input 1111 to the ultrasound scanning module 1103. These analog images are digitized via the ultrasound scanning module 1103 and stored in a computer memory 1113. Computer memory 1113 can then store the digitized 2-D images via image data transfer in a file storage device 1115, or, upon receipt of an appropriate user command from interface 1101, the 2-D images may be reconstructed via volume reconstruction software module 1105, as discussed in greater detail below. Once the 3-D image has been reconstructed in module 1105 and stored in computer memory 1113, upon receipt of appropriate user commands from user interface 1101, the volume viewer module 1107 manipulates the view perspective of the reconstructed 3-D image for output to a monitor (output to monitor module 1117).

According to the preferred embodiment, motor 31 (FIG. 4), 57 (FIG. 5), 73 (FIG. 7), 81 (FIGS. 8A and 8B) and 97 (FIG. 9) are precision motors which rotate their respective shafts with constant angular increment or velocity. Thus, when the 2-D images are acquired, they are equally spaced (i.e. either with constant angular intervals when sector or axial geometries are implemented, or with constant distance in the case of a linear geometry). In some cases the selected motor may include an internal position encoder to ensure shaft rotation at a constant angular velocity. One example of such a preferred motor is the Model C57-51 stepper motor manufactured by Compumotor (division of Parker Corporation).

Figure 12A:
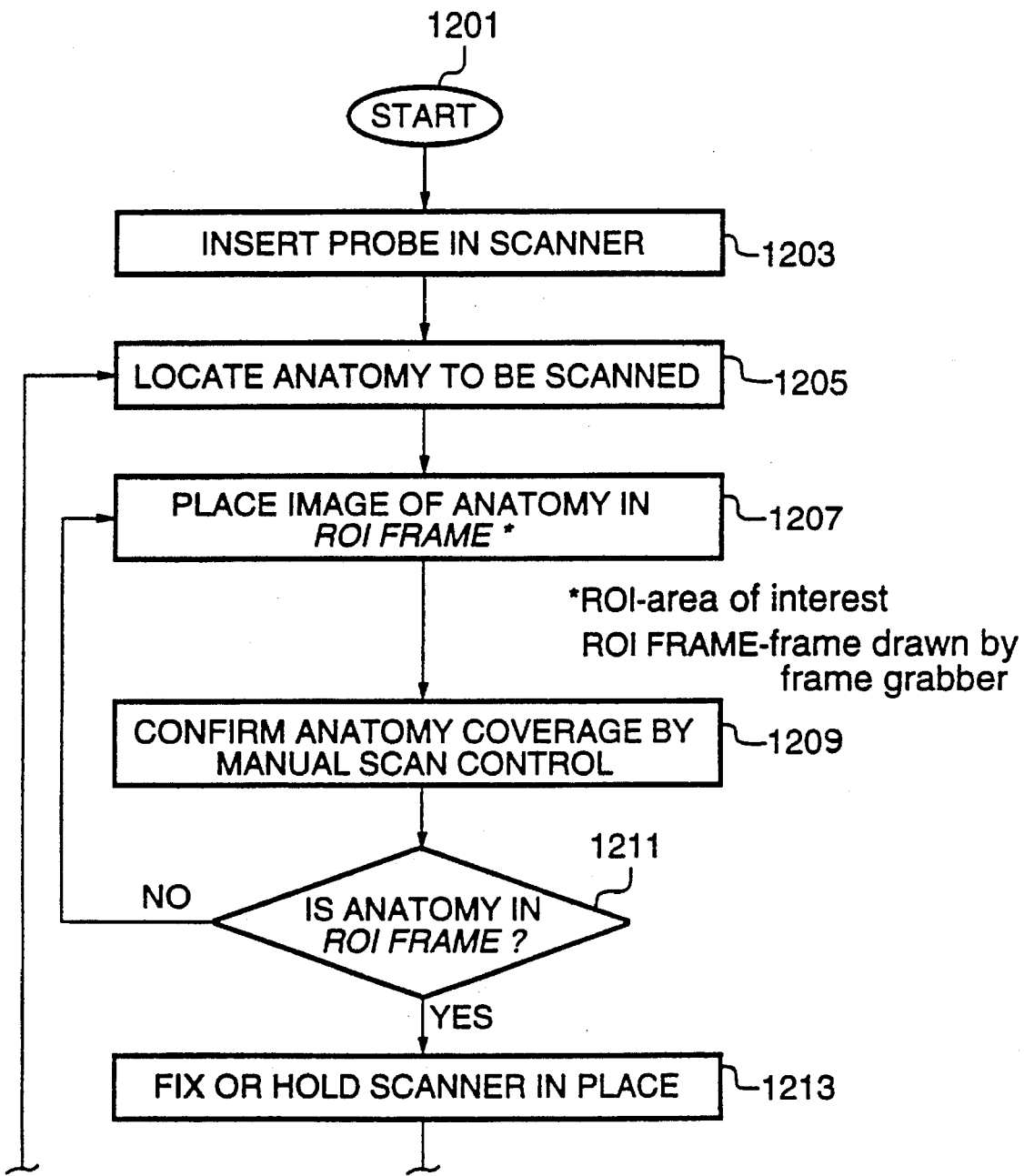
FIG. 12 is a flow chart showing operation of the 3-D ultrasound imaging system of the present invention.
Figure 12B:
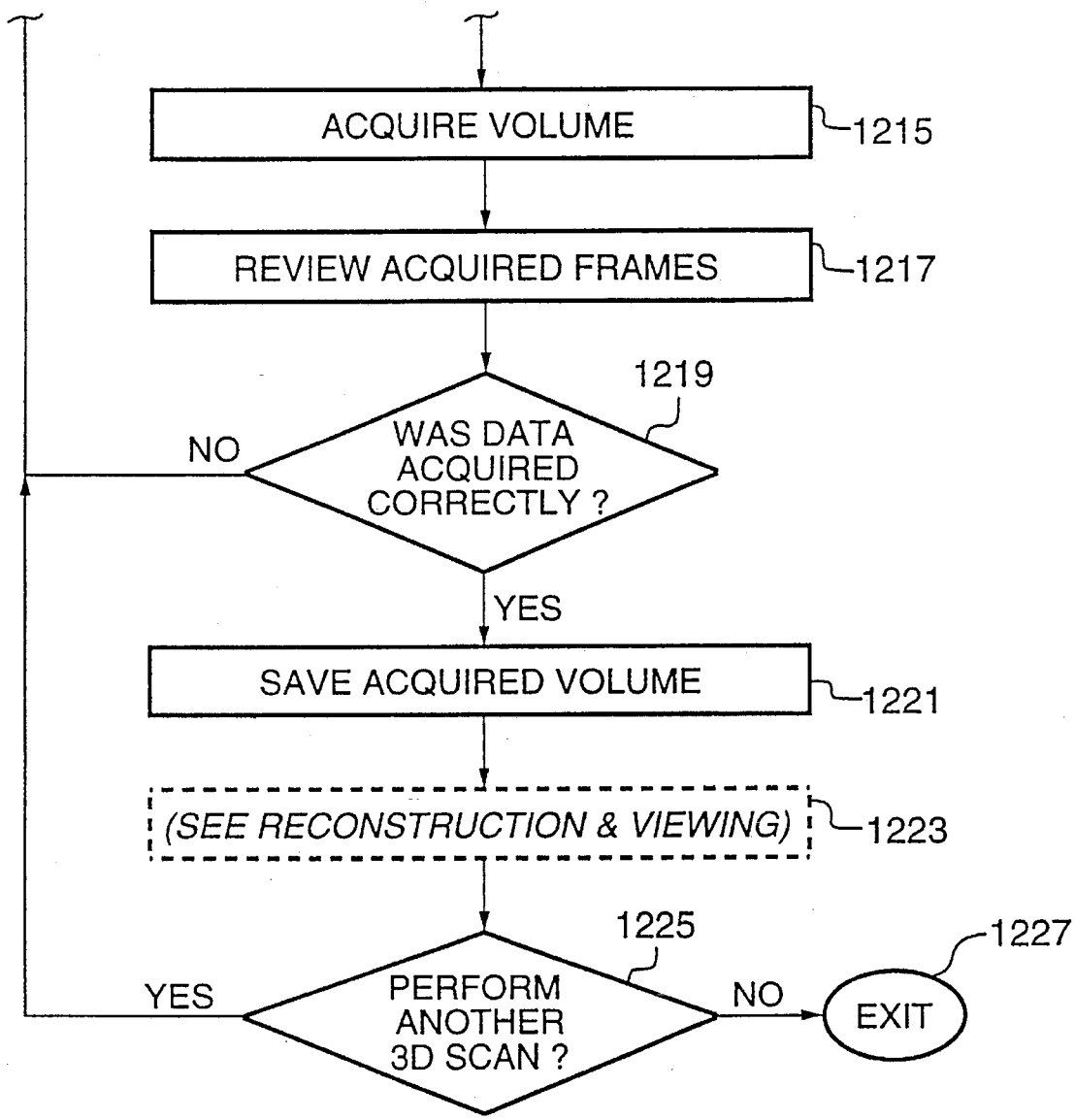

Turning now to FIG. 12, upon starting a typical 3-D ultrasound imaging procedure (start step 1201), the probe 1 is inserted into the scanner assembly (step 1203), the anatomy to be scanned is located (step 1205), and an image of the anatomy is placed in an ROI frame (step 1207). The ROI frame is a frame drawn on the output monitor by a frame grabber program executed by computer 11, where ROI represent an area of interest. Next, the user confirms the anatomy coverage by manual scan control (step 1209). If the anatomy is outside of the ROI frame, then operation returns to step 1207, otherwise, (step 1211) the operation proceeds to step 1213 wherein the user fixes or holds the probe scanner assembly in place. Next, in step 1215, a volume of image is acquired and the user may review the acquired frames in step 1217. If the data has been acquired incorrectly (step 1219), the process control returns to step 1205. Otherwise, process control proceeds to step 1221 in which the acquired volume is saved and stored to computer memory as a stack of 2-D images I(x,y,z) (see 1113 of FIG. 11). Next, the steps of reconstruction and viewing of the 3-D image are effected (step 1223 is discussed in greater detail below with reference to FIGS. 14–23). If the user wishes to perform another 3-D scan (step 1225), the process control returns to step 1205. Otherwise, the procedure is exited (step 1227).

Figure 13:
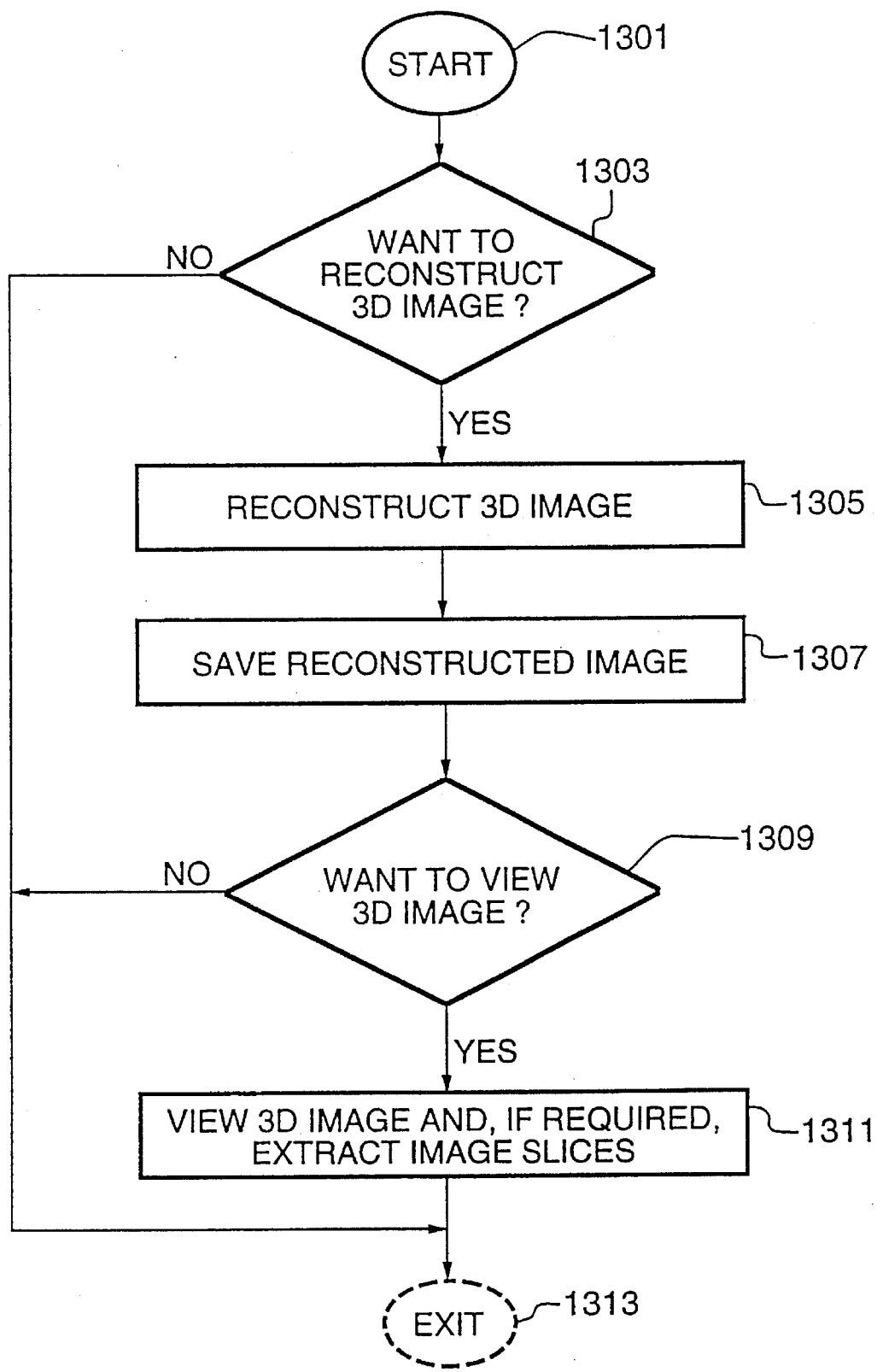
FIG. 13 is a flow chart showing details of the reconstruction and viewing steps of operating the 3-D imaging system of the present invention.
Figure 14:
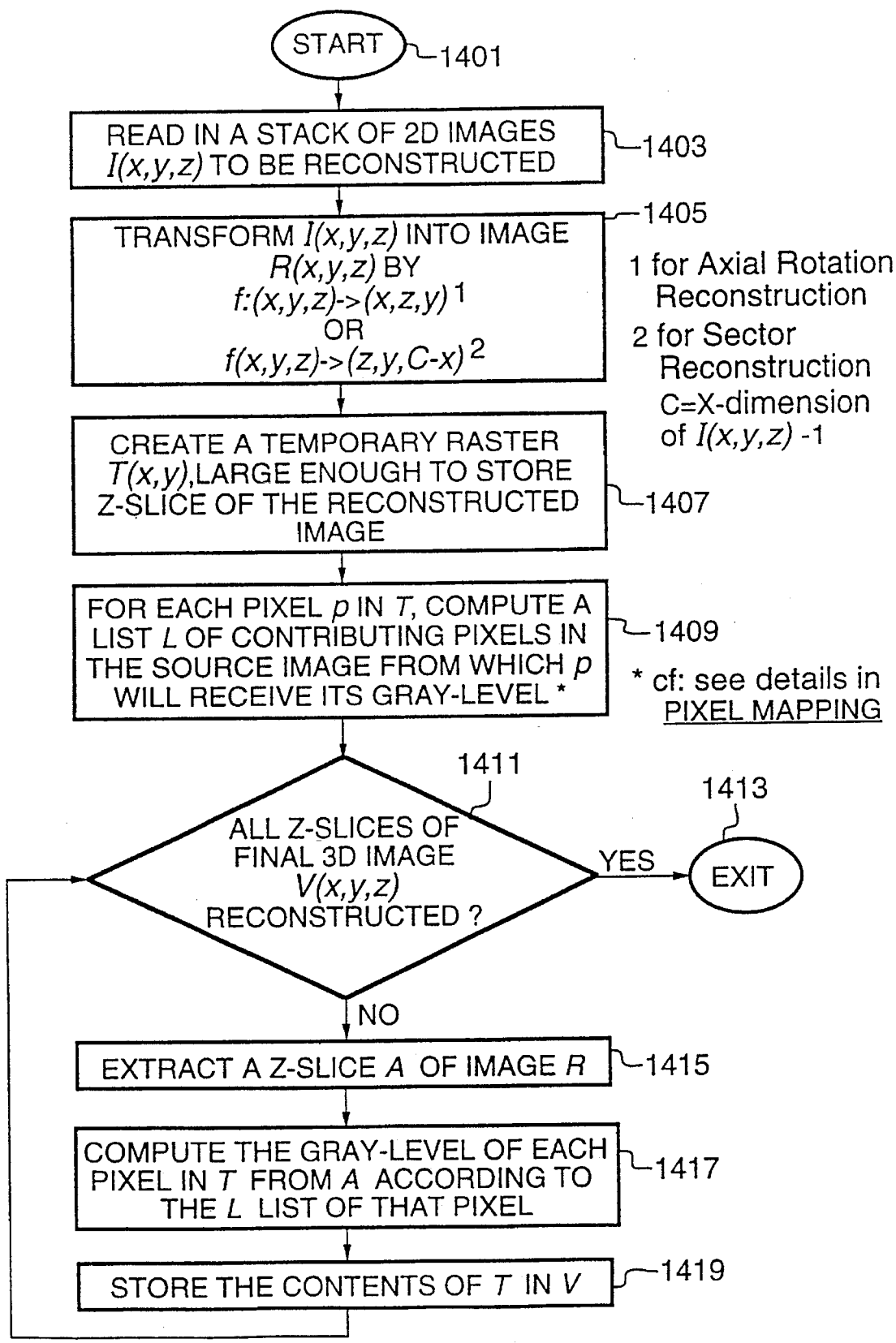
FIG. 14 is a flow chart showing details of 3-D image reconstruction according to the preferred embodiment.

The steps for utilizing the reconstruction and viewing algorithm discussed in greater detail below with reference to FIGS. 14–23, are shown in FIG. 13, beginning with a start step 1301. If the user does not wish to reconstruct a 3-D image (step 1303), then the user merely exits the system (step 1313). Otherwise, the system reconstructs the 3-D image (step 1305), and saves the reconstructed image to computer memory (step 1307). The user is then given the opportunity to view the 3-D image (step 1309). If the user does not elect to view the 3-D image, then process control returns to set 1303. However, if the user wishes to view the captured and reconstructed 3-D image, then the image is viewed and if required image slices may be extracted (step 1311). After viewing the 3-D image, the procedure is exited (step 1313).

Turning now to FIGS. 14–23, the 3-D image reconstruction algorithm of module 1105 (FIG. 11) is discussed in greater detail. After initializing the module (step 1401), the stack of 2-D images I(x,y,z) is retrieved from computer memory 1113 (step 1403). The stack of images I(x,y,z) is transformed into a resultant image R(x,y,z). For axial rotation reconstruction (i.e. the embodiment of FIGS. 10C and 10D), the transformation function is f: (x,y,z)→(x,z,y). For sector reconstruction, the transformation is effected by f: (x,y,z)→(z,y,C–x), where C is the x-dimension I(x,y,z)–1.

Figure 16A:
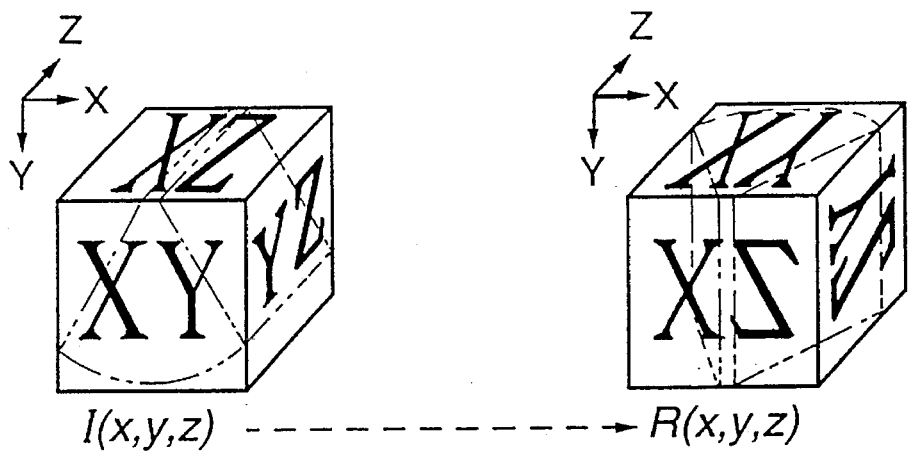
FIGS. 16A and 16B are reconstruction diagrams showing transformation of an input image captured by axial rotation and sector rotation, respectively.
Figure 16B:
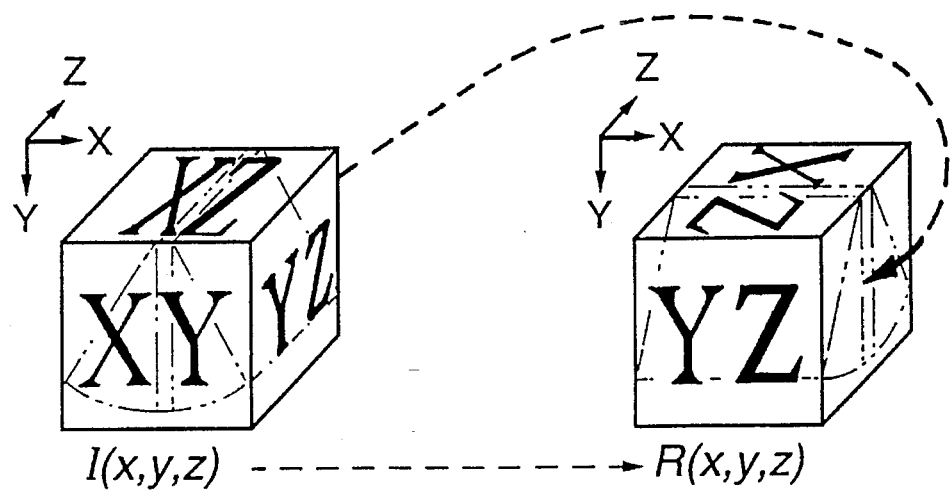

Considering the transformation of I(x,y,z) to R(x,y,z) for sector reconstruction, in order to access a vertical line of the image stored in computer memory 1113, the transformation is effected as shown in FIG. 16B to provide easy access to each vertical line of each image slice. The most efficient procedure for accessing each vertical line of the image is to do so on the zy-plane. Hence, as shown in FIG. 16B, the image is rotated so that 2-D images on the yz-plane are transformed to the xy-plane.

With respect to axial rotation (FIG. 16A), the same geometry of 2-D images is originally stored in computer memory 1113, except that instead of accessing vertical lines, for 3-D reconstruction the system captures horizontal lines. The horizontal 2-D image "slices" are accessed from top-to-bottom of the 3 D volume rather than from front-to-back, to provide greater speed of image reconstruction with the fewest number of calculations.

The transformations of step 1405 are conducted on a pixel-by-pixel basis, utilizing known methodologies.

Figure 17:
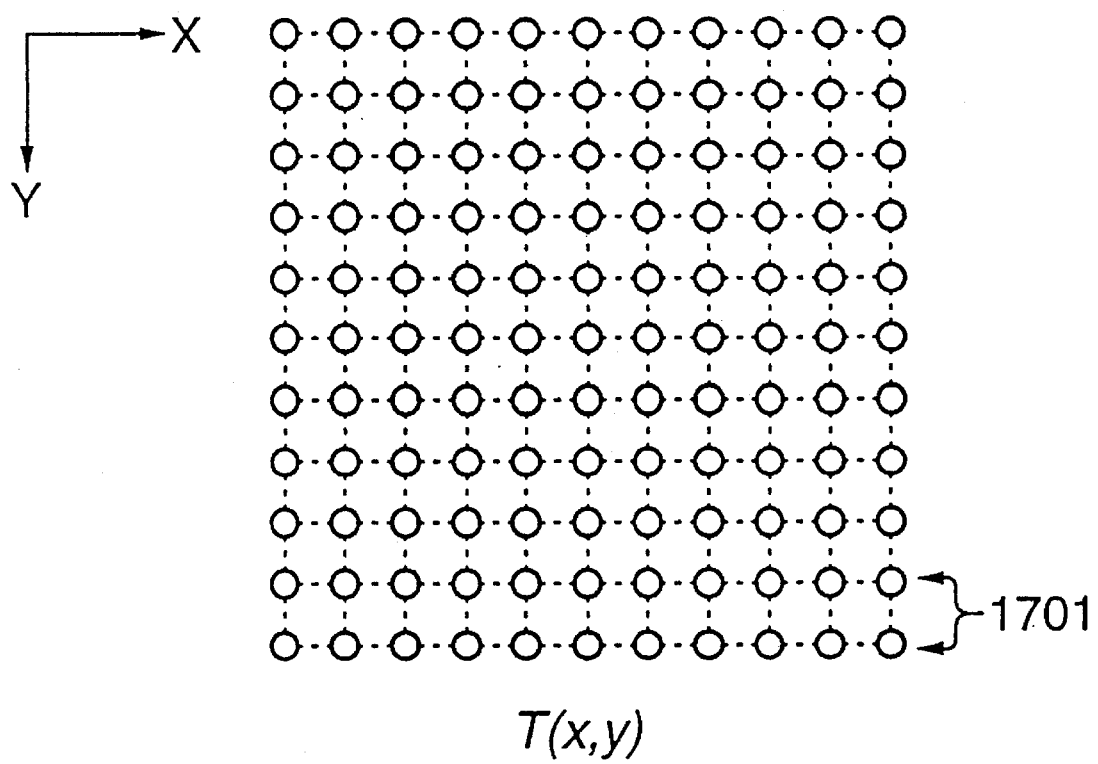
FIG. 17 is a reconstruction diagram schematically representing a temporary raster.

In step 1407, a temporary raster T(x,y) is created which must be large enough to store a z-slice of the reconstructed image. FIG. 17 shows a temporary raster T(x,y) comprising a plurality of grid points or pixels 1701. The temporary raster T(x,y) is used to hold a single z-slice of the reconstructed image, which is represented by a 3-D array V(x,y,z).

Upon creating the temporary raster T(x,y) all computer calculations are performed on the x,y-plane (i.e. on individual z-slices of the image). The temporary raster T(x,y) must be created to sufficiently large dimensions to accommodate the creation of bigger images in axial rotation geometries. For each pixel in the temporary raster T(x,y) the module must find the exact coordinate in the original slice of the resultant image R(x,y,z) (i.e. the exact color or grey level must be computed for each pixel in T from R).

Figure 18A:
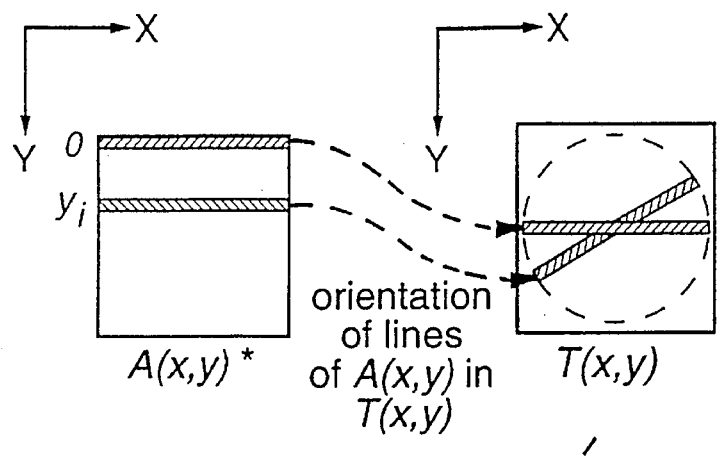
FIGS. 18A and 18B are reconstruction diagrams showing the computation of the contents of the temporary raster for an image captured by axial rotation.
Figure 18B:
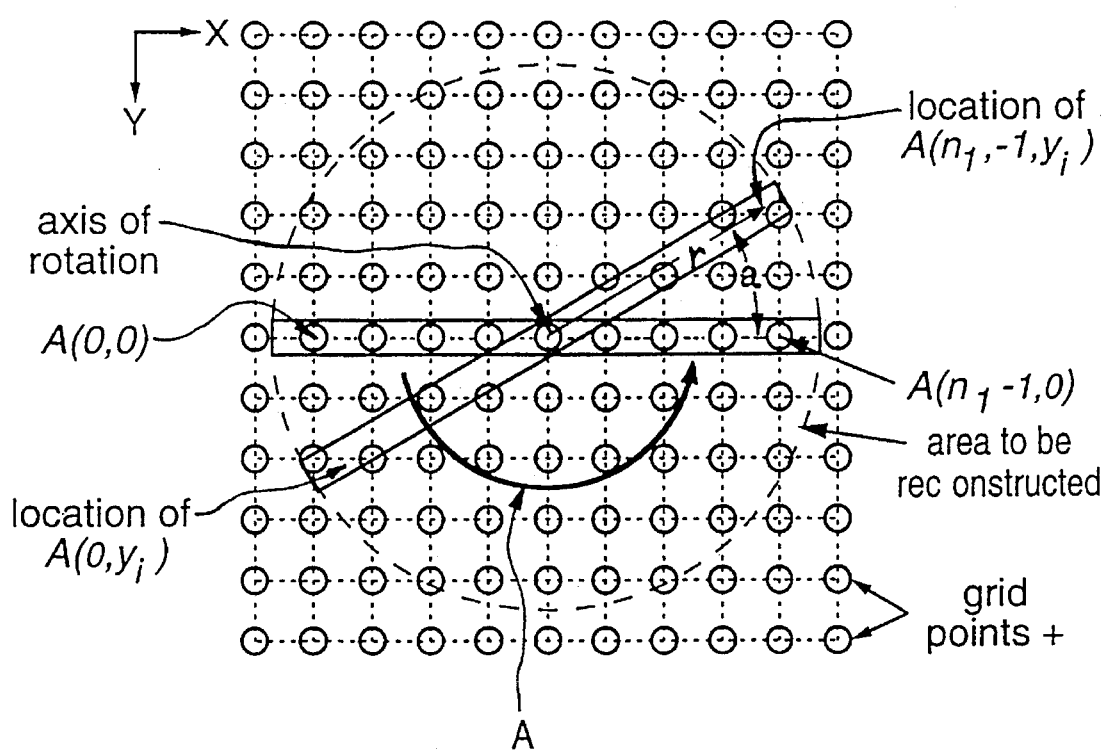

In step 1409, for each pixel p(x,y) in T(x,y) a list L(x,y) of contributing pixels is computed in the source image from which each such pixel receives a gray level, discussed in greater detail below with reference to FIG. 15. FIGS. 18A and 18B shown computation of the contents of temporary raster T(x,y) from a z-slice of the resultant image R(x,y,z), wherein the x-dimension of A(x,y) is $n_1$. For axial rotation, the geometry is such that there is a line which rotates according to a circular path to compute the original location for a pixel T, therefor the use of polar coordinates is adopted. Starting from the origin, the radial distance "r" from the pixel and the angle "a" are computed. After "r" and "a" are computed, indexing is used for each image slice in R since the location of the first horizontal line of the image is known. By using the angle "a" the module computes where the pixel should be located in R. Once the location of the pixel has been computed, one of either a "nearest neighbor algorithm" or an averaging algorithm or weighting function are used to approximate the appropriate gray-level for the pixel. The arrow A in FIG. 18B shows the direction with which the original images in I(x,y,z) were captured.

Figure 19A:
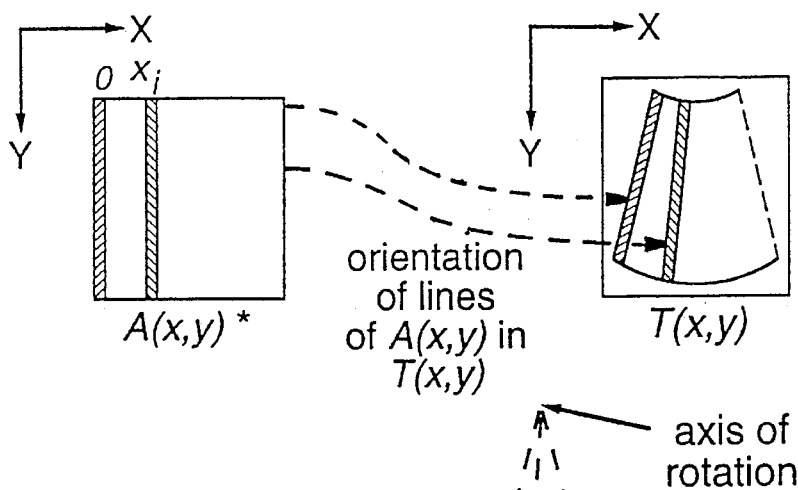
FIGS. 19A and 19B are reconstruction diagrams showing computation of the contents of the temporary raster for sector rotation.
Figure 19B:
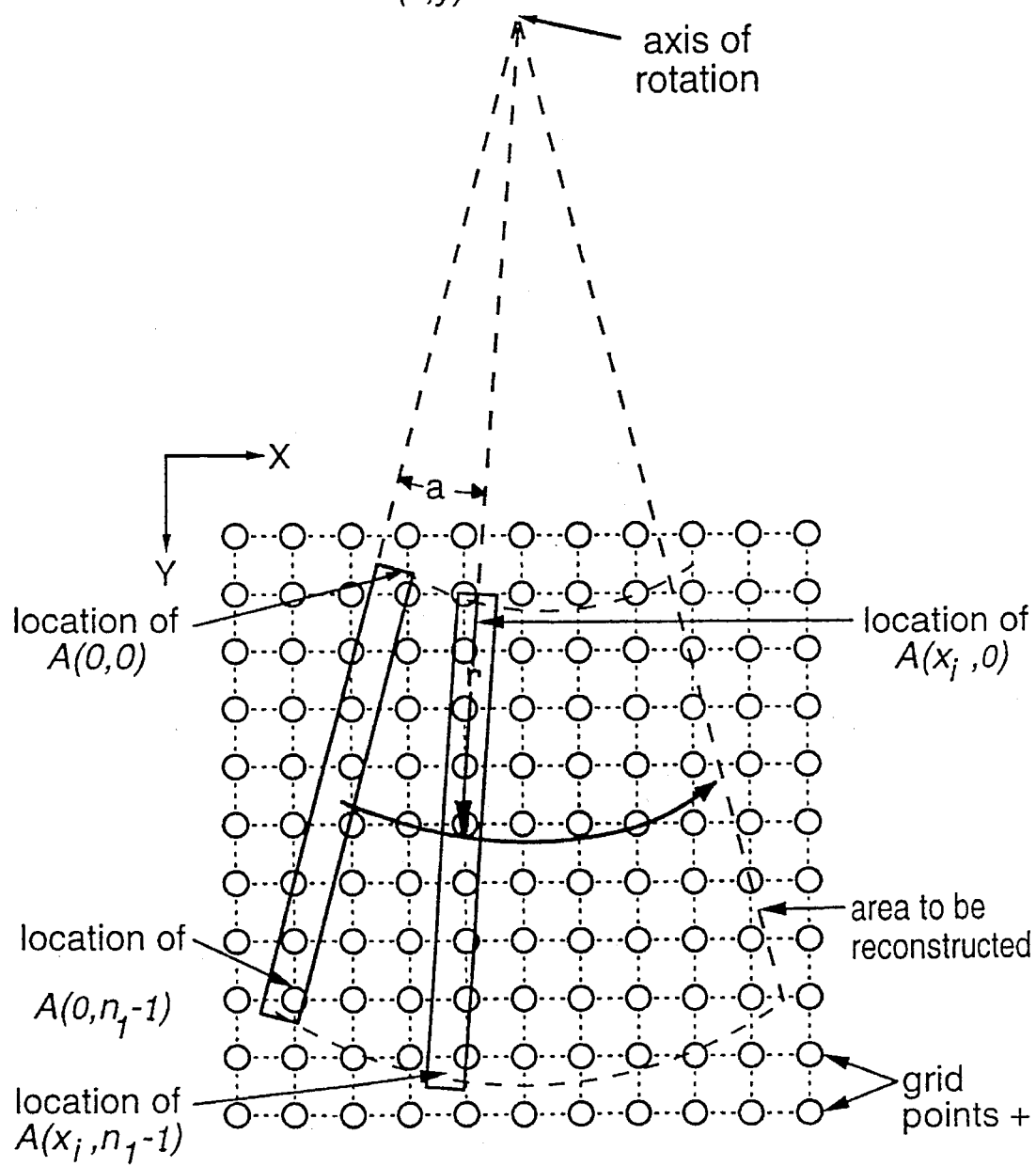

FIGS. 19A and 19B show the computation of contents of the temporary raster T(x,y) from A(x,y) for sector reconstruction.

For sector rotation, the geometry is similar to that of axial rotation except that the axis of rotation is outside of the image. As discussed above with reference to axial reconstruction, the angular displacement and distance of each pixel is computed from the first line of the image. However, a smaller value of "r" is used in sector reconstruction than the actual distance from the pixel to the axis of rotation since there is no need to extend the radius all of the way back to the axis of rotation. Using well known linear algebra techniques, the vector established by the calculated polar coordinates can be transformed to have the same origin (i.e. it is possible to ignore the axis of rotation outside of the image volume).

As shown in FIGS. 20A, 20B, 21A and 21B, the list L of $p(x_0, y_0)$ may contain some or all of the pixels neighbors in A(x,y), depending on the scheme adopted (i.e. nearest neighbor, averaging or interpolation of neighbors). In step 1411, the module queries whether all z-slices of the final 3-D image V(x,y,z) have been constructed. If the answer to the query is no, then a new z-slice A(x,y) is extracted from the resultant image R(x,y,z) and the grey level or color of each pixel T(x,y) from A(x,y) is computed according to the L list of that pixel by means of nearest neighbor, or averaging or interpolation of neighbor pixels (step 1417).

Figure 20A:
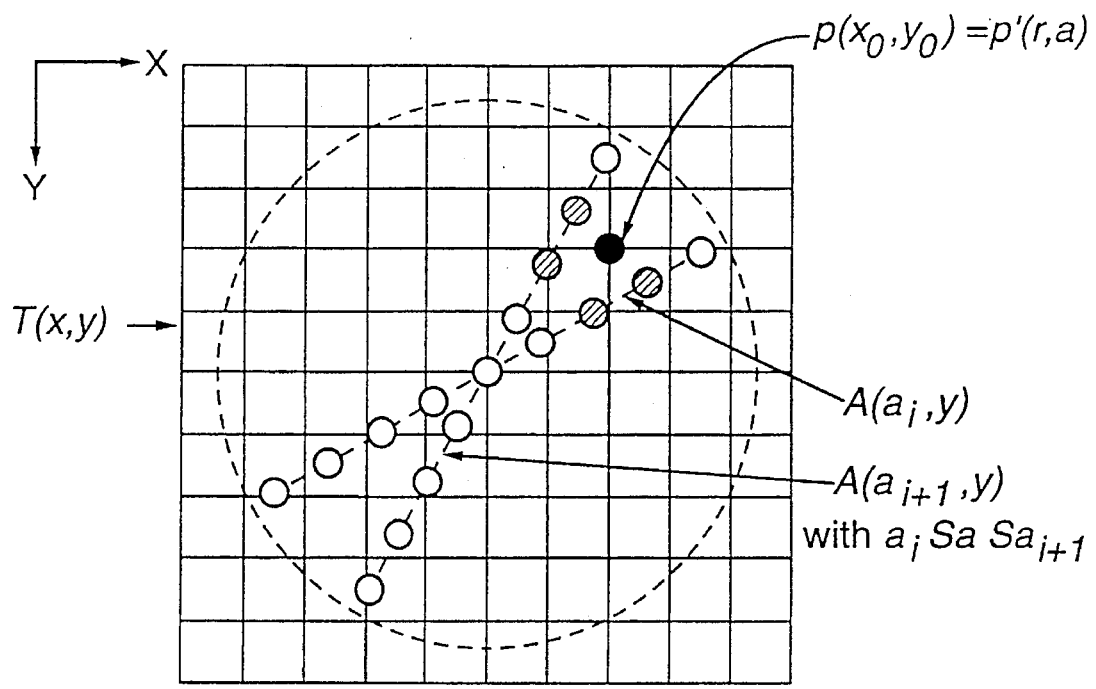
FIGS. 20A and 20B are reconstruction diagrams showing the creation of a list of contributing pixels in the temporary raster for an image captured by axial rotation.
Figure 20B:
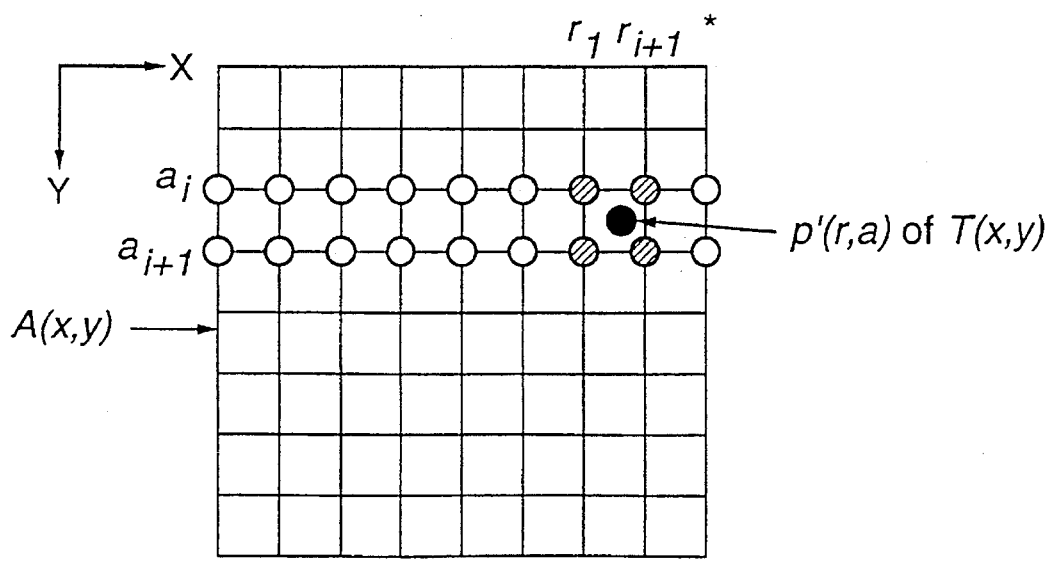
Figure 21A:
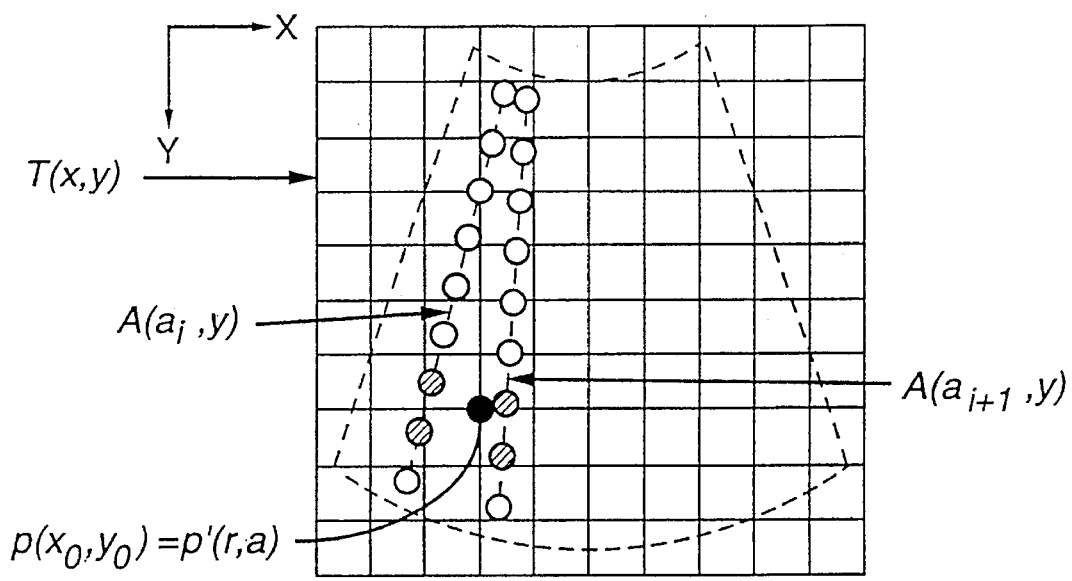
FIGS. 21A and 21B are reconstruction diagrams showing the creation of a list of contributing pixels in the temporary raster for an image captured by sector rotation.
Figure 21B:
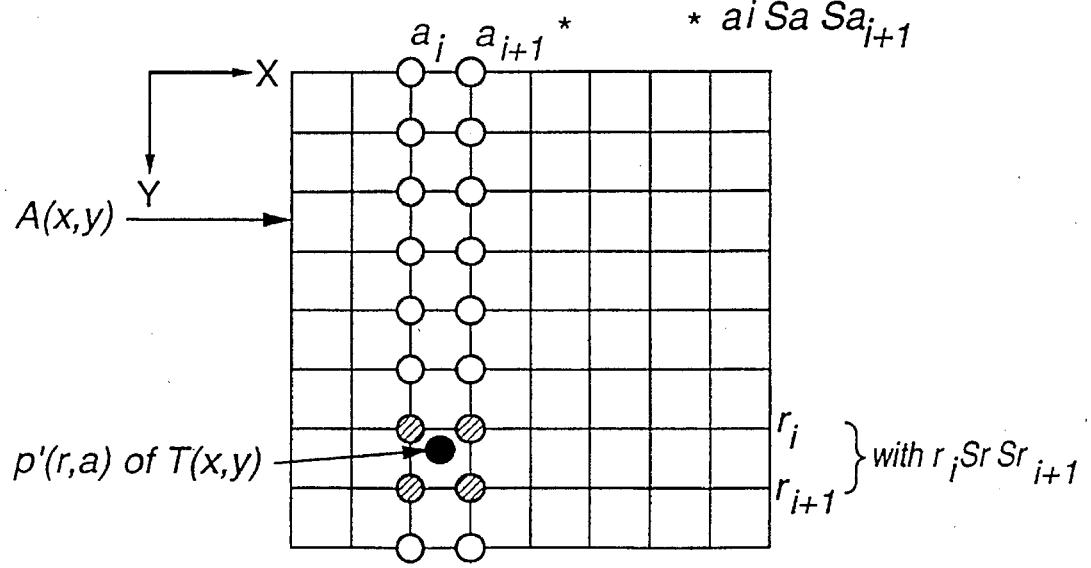

Once the list of neighbors has been computed for each pixel T, then the entire 3-D volume can be reconstructed. In particular, each slice in R is accessed and reconstruction is executed, one slice at a time according to the list of neighbors L. After finding the exact location of the pixel R, the list L of contributing pixels is computed. In FIGS. 20A and 21A, the location of the pixels is shown for axial rotation and sector rotation, respectively. Indexing is then performed to revert to the individual z-slice of R (referred to as A), which changes the geometry back to a rectangularly shaped image (FIGS. 20B and 21B). At this stage, all four neighbors of the pixel are accessed to determine the appropriate grey-level or color for the selected pixel of T(x,y).

Figure 22:
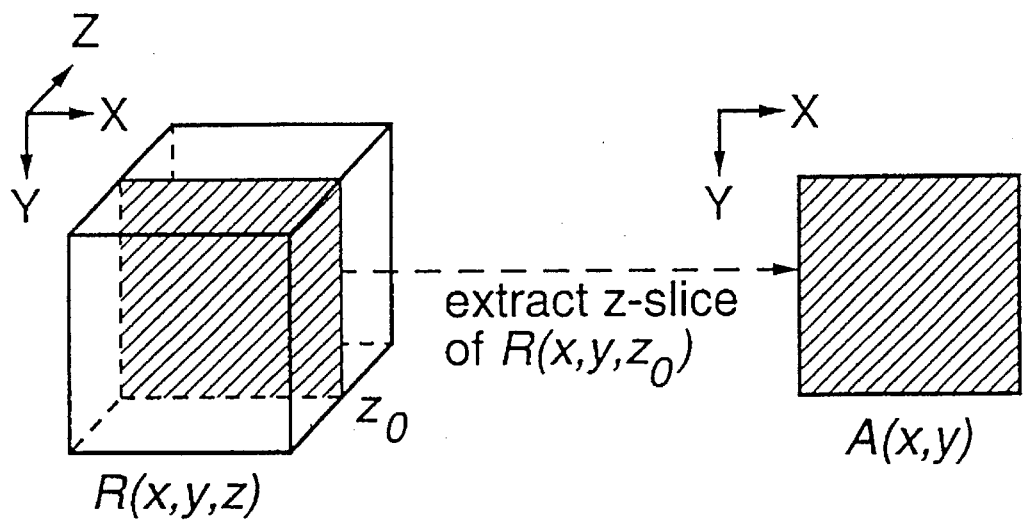
FIG. 22 is a reconstruction diagram showing extraction of a slice of a resultant image.
Figure 23:
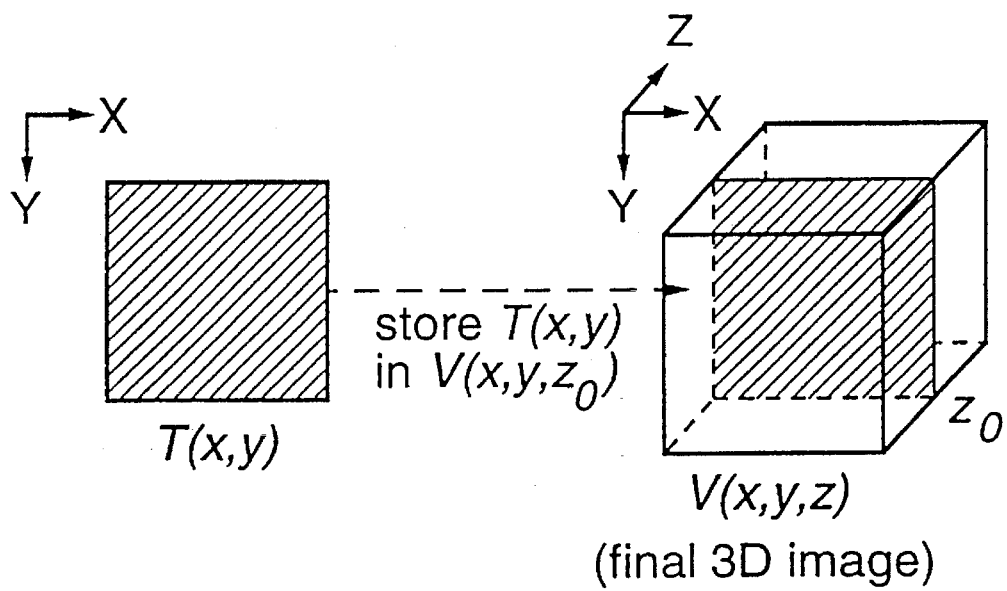
FIG. 23 is a reconstruction diagram showing the storage of the contents of the temporary raster in an array of output pixels forming a reconstructed 3-D image.

In FIG. 22, the z-slice A(x,y) of R(x,y,z) is extracted and the computation of step 1417 is effected to compute all values of the plane that are contributed by the resultant image R(x,y,z) for storage into the final volume. After finishing all slices of R(x,y,z), the reconstruction is complete and the contents of T(x,y) are stored in the final 3-D image V(x,y,z).

Steps 1411–1419 are re-executed until all z-slices of the final 3-D image have been reconstructed, after which the module is exited (step 1413).

Figure 15:
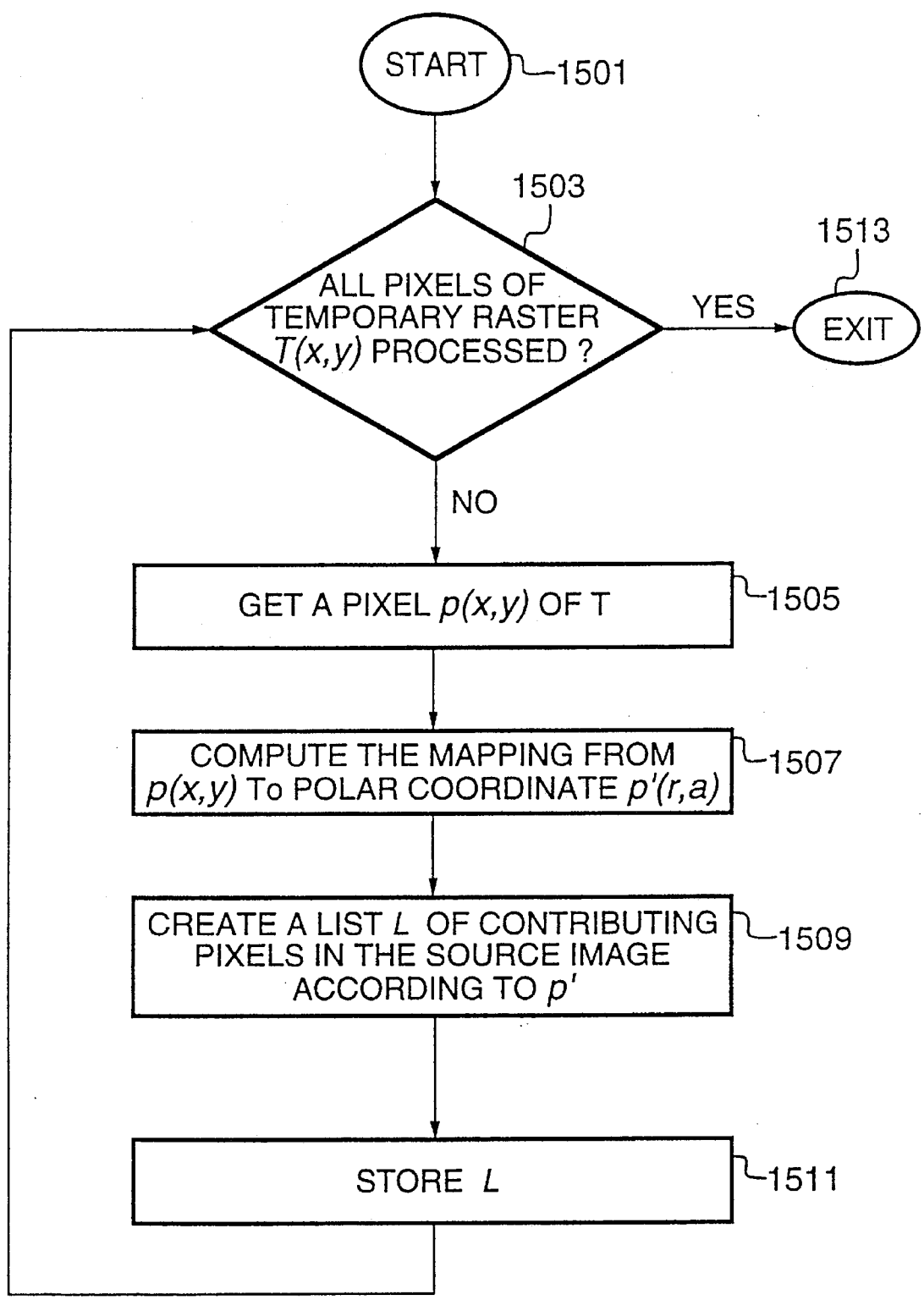
FIG. 15 is a flow chart showing details of the pixel mapping steps of the reconstruction process illustrated in FIG. 14.

Turning briefly to FIG. 15, the pixel mapping step 1409 is shown in greater detail as a sub-module.

The module is initiated at step 1501, following which the procedure queries whether all pixels of the temporary raster T(x,y) has been processed (step 1503).

If not, a pixel p(x,y) of the temporary raster T(x,y) is retrieved in step 1505. A mapping from p(x,y) to polar coordinates p'(r,a) is computed in step 1507 using the techniques discussed above with reference to FIGS. 18A, 18B, 19A and 19B.

Next, a list L(x,y) is created of the contributing pixels in the source image according to p'(r,a) (step 1509). The creation of this list is shown with reference to FIGS. 20A and 20B for axial rotation and 21A and 21B for sector reconstruction.

The list L(x,y) is then stored at step 1511 and process control is returned to the query of step 1503. Once all pixels of the temporary raster T(x,y) have been processed, the sub-module is exited at step 1513.

As discussed above, once the reconstruction has been completed and the reconstructed image array V(x,y,z) has been stored in computer memory 1113, the image may be viewed and manipulated in a well known manner utilizing volume viewer module 1107 (FIG. 11) (e.g. Analyzer™).

Other embodiments and modifications of the invention are possible within the sphere and scope defined by the claims appended hereto.

I claim:

1. A three-dimensional ultrasound system for use with an ultrasound probe connected to a clinical ultrasound machine and a computer for storing a succession of two-dimensional images generated by said clinical ultrasound machine represented by an array of pixels I(x,y,z), responsive to movement of said probe, the system comprising:

a) an assembly for mounting said probe adjacent an organ to be examined and for moving said assembly such that said probe scans said organ to be examined in a single sweep, thereby resulting in generation of said succession of two-dimensional images by said clinical ultrasound machine and storage in said computer of said images represented by said array of pixels I(x,y,z); and b) controller means in said computer for (i) controlling movement of said assembly such that said probe sweeps out a predetermined volume of said organ to be examined and (ii) reconstructing said two-dimensional images represented by said array of pixels I(x,y,z) to form a reconstructed three-dimensional image represented by an array of output pixels V(x,y,z).

2. The three-dimensional ultrasound system of claim 1, wherein said assembly further includes:

c) motor means having an output shaft which rotates about an axis of rotation thereof under control of said controller means; and d) adapter means for mounting said probe at a predetermined position relative to said axis of rotation such that said probe sweeps out said predetermined volume of said organ to be examined upon rotation of said output shaft.

3. The three-dimensional ultrasound system of claim 2, wherein adapter means is connected to said output shaft in parallel with said axis of rotation such that said predetermined volume is a cylinder.

4. The three-dimensional ultrasound system of claim 3, wherein said controller means further comprises:

e) means for transforming said array I(x,y,z) into resultant array R(x,y,z) according to the transformation f:(x,y,z)→(x,z,y);

f) means for creating a temporary raster T(x,y,) for storing a single z-slice of said reconstructed three-dimensional image;

g) means for computing a list L of contributing pixels from a z-slice A(x,y) of the resultant array R(x,y,z) for each pixel p(x,y) in T(x,y), and in response storing said list L;

h) means for extracting successive z-slices A(x,y) of said resultant array R(x,y,z);

i) means for computing one of either a gray-level or color for each pixel p(x,y) in T(x,y) from A(x,y) according to the list L for each said pixel p(x,y) and storing said one of either gay-level or color for each said pixel p(x,y) in said temporary raster T(x,y); and h) means for storing the contents of said temporary raster T(x,y) in said array of output pixels V(x,y,z).

5. The three-dimensional ultrasound system of claim 4, wherein said means for computing said list L further comprises:

j) means for retrieving each said pixel p(x,y);

k) means for converting p(x,y) to a polar coordinate p'(r,a);

l) means for creating said list L of contributing pixels according to p'(r,a); and m) means for storing L.

6. The three-dimensional ultrasound system of claim 4, wherein said means for computing said gray-level further comprises one of either means for averaging, means for interpolating or means for selecting a nearest one of said contributing pixels to each said pixel p(x,y).

7. The three-dimensional ultrasound system of claim 2, wherein said adapter means is connected to said output shaft orthogonally to said axis of rotation such that said predetermined volume is a cylindrical sector.

8. The three-dimensional ultrasound system of claim 7, wherein said controller means further comprises:

e) means for transforming said array I(x,y,z) into a resultant array R(x,y,z) according to the transformation f:(x,y,z)→(z,y,C−x), where C is the x dimension of I(x,y,z) minus 1;

f) means for creating a temporary raster T(x,y) for storing a single z-slice of said reconstructed three-dimensional image;

g) means for computing a list L of contributing pixels from a z-slice A(x,y) of said resultant array R(x,y,z) for each pixel p(x,y) in said temporary raster T(x,y), and in response storing said list L;

h) means for extracting successive z-slices A(x,y) of said resultant array R(x,y,z);

i) means for computing one of either a gray-level or color for each pixel p(x,y) in said temporary raster T(x,y) from said z-slice A(x,y) according to said list L for each said pixel p(x,y) and storing said one of either gray-level or color for each said pixel p(x,y) in said temporary raster T(x,y); and j) means for storing the contents of said temporary raster T(x,y) in said array of output pixels V(x,y,z).

9. The three-dimensional ultrasound system of claim 8, wherein said means for computing said list L further comprises:

j) means for retrieving each said pixel p(x,y);
k) means for converting p(x,y) to a polar coordinate p'(r,a);
l) means for creating said list L of contributing pixels according to said polar coordinate p'(r,a); and
m) means for storing said list L.

10. The three-dimensional ultrasound system of claim 8, wherein said means for computing said gray-level further comprises one of either means for averaging, means for interpolating or means for selecting a nearest one of said contributing pixels to each said pixel p(x,y).

11. The three-dimensional ultrasound system of claim 2, wherein said adapter means is connected to said output shaft for longitudinal translation thereon, such that said predetermined volume is a parallelepiped.

12. The three-dimensional ultrasound system of claim 1 wherein said organ is an eye.

13. The three-dimensional ultrasound system of claim 1 wherein said organ is a prostate.

14. The three-dimensional ultrasound system of claim 1 wherein said organ is a female breast.

15. The three-dimensional ultrasound system of claim 1 wherein said organ is a heart.

16. The three-dimensional ultrasound system of claim 1 wherein said organ comprises arteries and veins.

17. The three-dimensional ultrasound system of claim 1 wherein said organ is a kidney.

18. The three-dimensional ultrasound system of claim 1 wherein said organ is a liver.

19. A three-dimensional ultrasound system for use with an ultrasound probe connected to a clinical ultrasound machine and a computer for storing a succession of two-dimensional images generated by the clinical ultrasound machine represented by an array of pixels I(x,y,z), responsive to movement of the probe, said system comprising:

an assembly for mounting the probe adjacent an organ to be examined and for moving said assembly such that the probe scans said organ to be examined in a single sweep, thereby resulting in generation of the succession of two-dimensional images by the clinical ultrasound machine in storage in the computer of the two-dimensional images represented by the array of pixels I(x,y,z);

controller means in the computer for controlling movement of said assembly such that the probe sweeps out a predetermined volume of the organ to be examined and for reconstructing the two-dimensional images represented by the array of pixels I(x,y,z) to form a reconstructed three-dimensional image represented by an array of output pixels V(x,y,z);

motor means having an output shaft which rotates about an axis of rotation thereof under control of said controller means;

adapter means for mounting the probe at a predetermined position relative to said axis of rotation such that the probe sweeps out the predetermined volume of the organ to be examined upon rotation of said output shaft, said adapter means being connected to said output shaft in parallel with said axis of rotation such that said predetermined volume is a cone;

means for transforming the array I(x,y,z) into a resultant array R(x,y,z) according to the transformation f:(x,y,z)→(x,z,y);

means for creating a temporary raster T(x,y) for storing a single z-slice of said reconstructed three-dimensional image;

means for computing a list L of contributing pixels from a z-slice A(x,y) of said resultant array R(x,y,z) for each pixel p(x,y) in said temporary raster T(x,y) and in response, storing said list L;

means for extracting excessive z-slices A(x,y) of said resultant array R(x,y,z);

means for computing one of a gray-level and color for each pixel p(x,y) in said temporary raster T(x,y) from said z-slice A(x,y) according to said list L for each said pixel array p(x,y) and storing said one of said gray-level and color for each said pixel p(x,y) in said temporary raster T(x,y); and means for storing the contents of said temporary raster T(x,y) in said array of output pixels V(x,y,z).

20. The three-dimensional ultrasound system of claim 19, wherein said means for computing said list L further comprises:

means for retrieving each said pixel p(x,y);
means for converting said pixel p(x,y) to a polar coordinate p'(r,a);
means for creating said list L of contributing pixels according to said polar coordinate p'(r,a); and
means for storing said list L.

21. The three-dimensional ultrasound system of claim 19, wherein said means for computing said gray level further comprises one of either means for averaging, means for interpolating and means for selecting a nearest one of said contributing pixels to each said pixel p(x,y).

22. The three-dimensional ultrasound system of claim 19, wherein said means for computing said list L further comprises:

means for retrieving each said pixel p(x,y);
means for converting said pixel p(x,y) to a polar coordinate p'(r,a);
means for creating said list L of contributing pixels according to said polar coordinate p'(r,a); and
means for storing said list L.

23. The three-dimensional ultrasound system of claim 19, wherein said means for computing said gray-level further comprises one of either means for averaging, means for interpolating, and means for selecting a nearest one of said contributing pixels to each said pixel p(x,y).

24. A three-dimensional ultrasound system for use with an ultrasound probe connected to a clinical ultrasound machine and a computer for storing a succession of two-dimensional images generated by the clinical ultrasound machine represented by an array of pixels I(x,y,z), responsive to movement of the probe, said system comprising:

an assembly for mounting the probe adjacent an organ to be examined and for moving said assembly such that the probe scans said organ to be examined in a single sweep, thereby resulting in generation of the succession of two-dimensional images by the clinical ultrasound machine in storage in the computer of the two-dimensional images represented by the array of pixels I(x,y,z);

controller means in the computer for controlling movement of said assembly such that the probe sweeps out a predetermined volume of said organ to be examined and for reconstructing said two-dimensional images represented by the array of pixels I(x,y,z) to form a reconstructed three-dimensional image represented by an array of output pixels V(x,y,z);

motor means having an output shaft which rotates about an axis of rotation thereof under control of said controller means;

adapter means for mounting the probe at a predetermined position relative to said axis of rotation such that the probe sweeps out said predetermined volume of said organ to be examined upon rotation of said output shaft, said adapter means being connected to said output shaft orthogonally to said axis of rotation such that said predetermined volume is a cylindrical section;

means for transforming the array I(x,y,z) into a resultant array R(x,y,z) according to a transformation f:(x,y,z)→ (z,y,C−x), where C is an x dimension of the array I(x,y,z) minus 1;

means for creating a temporary raster T(x,y) for storing a single z-slice A(x,y) of said reconstructed three-dimensional image;

means for computing a list L of contributing pixels from said z-slice A(x,y) of said resultant array R(x,y,z) for each pixel p(x,y) in said temporary raster T(x,y), and in response, storing said list L;

means for extracting successive z-slices A(x,y) of said resultant array R(x,y,z);

means for computing one of a gray-level and color for each pixel p(x,y) in said temporary raster T(x,y) from said z-slice A(x,y) according to said list L for each said pixel p(x,y) and storing said one of said gray-level and color for each said pixel p(x,y) in said temporary raster T(x,y); and means for storing the contents of said temporary raster T(x,y) in said array of output pixels V(x,y,z).

25. A method for converting a succession of two-dimensional images of a target volume represented by an array of pixels I(x,y,z) into a three-dimensional image represented by a volumetric image array V(x,y,z) comprising the steps of:

(a) transforming said array of pixels I(x,y,z) into an image array R(x,y,z) so that each z-slice A(x,y) of the image array R(x,y,z) provides sufficient image data to construct an image slice;

(b) extracting a z-slice A(x,y) of the image array R(x,y,z) and computing the position of each pixel of the z-slice A(x,y) in a volumetric image array V(x,y,z);

(c) mapping one of a gray-level and color of the pixels of the z-slice A(x,y) into corresponding pixels of the volumetric image array V(x,y,z); and (d) repeating steps b) and c) until all z-slices A(x,y) of the image array R(x,y,z) have been processed to complete the volumetric image array V(x,y,z).

26. A system for converting a succession of two-dimensional images of a target volume represented by an array of pixels I(x,y,z) into a three-dimensional image represented by a volumetric image array V(x,y,z) comprising:

means for transforming said array of pixels I(x,y,z) into an image array R(x,y,z) so that each z-slice A(x,y) of said image array R(x,y,z) provides sufficient image data to construct an image slice;

means for extracting each z-slice A(x,y) of said image array R(x,y,z) and computing the position of each pixel of each z-slice A(x,y) in a volumetric image array V(x,y,z);

means for computing and storing one of a gray-level and color for each of the pixels of each z-slice A(x,y); and means for mapping said computed gray-levels or colors into corresponding pixels of said volumetric image array V(x,y,z).

27. A three-dimensional imaging system for acquiring a succession of two-dimensional images of a target volume represented by an array of pixels I(x,y,z) into a three-dimensional image represented by a volumetric image array V(x,y,z) comprising:

means for scanning the target volume and generating a succession of two-dimensional images thereof; and processing means for communicating with said scanning means, said processing means including:

means for converting the succession of two-dimensional images of the target volume into an array of pixels I(x,y,z);

means for transforming said array of pixels I(x,y,z) into an image array R(x,y,z) so that each z-slice A(x,y) of said image array R(x,y,z) provides sufficient image data to construct an image slice;

means for extracting each z-slice A(x,y) of said image array R(x,y,z) and computing the position of each of the pixels of each z-slice A(x,y) in a volumetric image array;

means for computing and storing one of a gray-level and color for each of the pixels of each z-slice A(x,y); and means for mapping one of said computed gray-level and color for each of the pixels of each z-slice A(x,y) into corresponding pixels of the volumetric image array V(x,y,z).

28. A three-dimensional imaging system as claimed in claim 27, wherein said scanning means includes: an ultrasound probe movable to scan the target volume; and a clinical ultrasound machine connected to said ultrasound probe to generate the succession of two-dimensional images.

* * * * *